United States Patent [19]
Kensil et al.

[11] Patent Number: 5,443,829
[45] Date of Patent: * Aug. 22, 1995

[54] **MODIFIED SAPONINS ISOLATED FROM *QUILLAJA* SAPONARIA**

[75] Inventors: Charlotte A. Kensil, Milford; Sean Soltysik, Worcester, both of Mass.; Dante J. Marciani, Birmingham, Ala.

[73] Assignee: Cambridge Biotech Corporation, Worcester, Mass.

[ * ] Notice: The portion of the term of this patent subsequent to Dec. 28, 2010 has been disclaimed.

[21] Appl. No.: 126,190

[22] Filed: Sep. 24, 1993

Related U.S. Application Data

[63] Continuation-in-part of Ser. No. 906,870, Jul. 2, 1992, Pat. No. 5,273,965.

[51] Int. Cl.$^6$ .................. A61K 35/78; A01N 65/00; A01N 43/04; A01N 45/00
[52] U.S. Cl. .................. 424/195.1; 514/25; 514/26; 514/33; 514/35; 514/160; 514/171
[58] Field of Search .............. 424/195.1; 514/35, 160, 514/169, 171, 25, 26, 33

[56] References Cited

U.S. PATENT DOCUMENTS

| | | | |
|---|---|---|---|
| 4,335,113 | 6/1982 | Combier et al. | 424/180 |
| 4,443,432 | 4/1984 | Garabedian et al. | 424/127 |
| 4,548,922 | 10/1985 | Carey et al. | 514/4 |
| 4,550,022 | 10/1985 | Garabedian et al. | 424/127 |
| 4,938,970 | 7/1990 | Hustead et al. | 424/678 |
| 4,985,253 | 1/1991 | Fujioka et al. | 424/488 |
| 5,057,540 | 10/1991 | Kensil et al. | 514/25 |
| 5,118,676 | 6/1992 | Minaskanian et al. | 514/183 |
| 5,118,692 | 6/1992 | Peck | 516/317 |
| 5,166,139 | 11/1992 | Bombardelli et al. | 514/26 |
| 5,182,258 | 1/1993 | Chiou | 514/3 |

FOREIGN PATENT DOCUMENTS 62126135 6/1987 Japan.
2064320 6/1981 United Kingdom.
88/09336 12/1988 WIPO.

OTHER PUBLICATIONS

Whitmore et al., Relative Effects of Different Surfactants on Intestinal Absorption and the Release of Proteins and Phospholipide. . . , *Journal of Pharmaceutical Pharmacology* 31:277–283 (1979).

Moore, J. A. et al., "Delivery Systems for Recombinant Methionyl Human Growth", *Delivery Systems for Peptide Drugs*, Davis, S. S. et al. (eds.), pp. 317–329, Plenum Press New York (1986).

Moses et al., Insulin Administered Intranasally as an Insulin–Bile Salt Aerosol, Effectiveness and Reproducibility in Normal and Diabetic Subjects, *Diabetes* 32:1040–1047 (1983).

Pillion et al., Systemic Absorption of Insulin Delivered Topically to the Rat Eye, *Investigative Opthalmology & Visual Science* 32:3021–3027 (1991).

Longenecker et al., Effects of Sodium Taurodihydrofusidate on Nasal Absorption of Insulin in Sheep, *Journal of Pharmaceutical Sciences* 76:351–355 (1987).

Maitani et al., Intanasal Administration of β–Interferon in Rabbits, *Drug Design and Delivery* 1:65–70 (1986).

Martin et al., Membrane Damage by Bile Salts: The Protective Function of Phospholipids, *Journal of Pharmaceutical Pharmacology* 31:754–759 (1981).

Kensil et al., Separation and Characterization of Sapo-
(List continued on next page.)

Primary Examiner—Marian C. Knode
Assistant Examiner—Kristin K. Larson
Attorney, Agent, or Firm—Sterne, Kessler, Goldstein & Fox

[57] ABSTRACT

Disclosed herein are modified saponins or fractions thereof obtainable by modification of a crude *Quillaja saponaria* extract or by modification of purified saponins obtainable from a crude *Quillaja saponaria* extract useful in pharmaceutical compositions for enhancing the transport of pharmacologically active substances across mucous membranes of an animal. Also disclosed are modified saponins having reduced irritability wherein the aldehyde group is reduced and the fatty acid moiety may be removed by hydrolysis. Also disclosed are pharmaceutical compositions comprising the modified saponins of the invention.

22 Claims, 23 Drawing Sheets

OTHER PUBLICATIONS nins with Adjuvant Activity from *Quillaja saponaria* Molina Cortex, *Journal of Immunology* 146:431-437 (1991).

Kimura et al., Mechanisms of Toxicities of Some Detergents Added to a Diet and of the Ameliorating Effect of Dietary Fiber in the Rat, *Journal of Nutrition Science Vitaminology* 28:483-489 (1982).

Lee et al., Intranasal Delivery of Proteins and Peptides, *BioPharm.* 30-37 (Apr. 1988).

Hirai et al., Nasal Absorption of Insulin in Dogs, *Diabetes* 27:296-299 (1978).

Hirai et al., Effect of Surfactants on the Nasal Absorption of Insulin in Rats, *International Journal of Pharmaceutics* 9:165-172 (1981).

Hirai et al., Mechanisms for the Enhancement of the Nasal Absorption of Insulin by Surfactants, *International Journal of Pharmaceutics* 9:173-184 (1981).

Higuchi et al., Structures of Compounds Derived from the Acyl Moieties of Quillajasaponin, *Phyto-chemistry* 26:2357-2360 (1987).

Higuchi et al., An Acylated Triterpenoid Saponin from *Quillaja Saponaria*, *Phytochemistry* 27:1165-1168 (1988).

Higuchi et al., Structure of Desacylsaponins Obtained from the Bark of *Quillaja Saponaria*, *Phytochemistry* 26:229-235 (1987).

Chiou et al., Improvement of Systemic Absorption of Insulin through Eyes with Absorption Enhancers, *Journal of Pharmaceutical Sciences* 78:815-818 (1989).

Chiou et al., Reduction of Blood Glucose Concentration with Insulin Eye Drops, *Diabetes Care* 11:750-751 (1988).

Chiou et al., Systemic Delivery of Insulin through Eyes to Lower the Glucose Concentration, *Journal of Ocular Pharmacology* 5:81-91 (1989).

Wu, J. et al., "The Journal of Immunology," vol. 148(5), pp. 1519-1525, Mar. 1, 1992.

Kensil, P., et al., "The FASEB Journal, " abstracts, #2190, p. A2071, Jun. 4-7, 1990 (abs).

Kensil, C. R. et al., Structure/Function Relationship in Adjuvants from *Quillaja* saponaria Molina, in Vaccines 92, F. Brown et al. (ed.), 1992 (pp. 35-40).

Maharaj, I. et al., Immune Responses of Mice to Inactivated Rabies Vaccine Administered Orally: Potentiation by *Quillaja saponin*, *Can. J. Microbiol.* 32: 414-420 (1986).

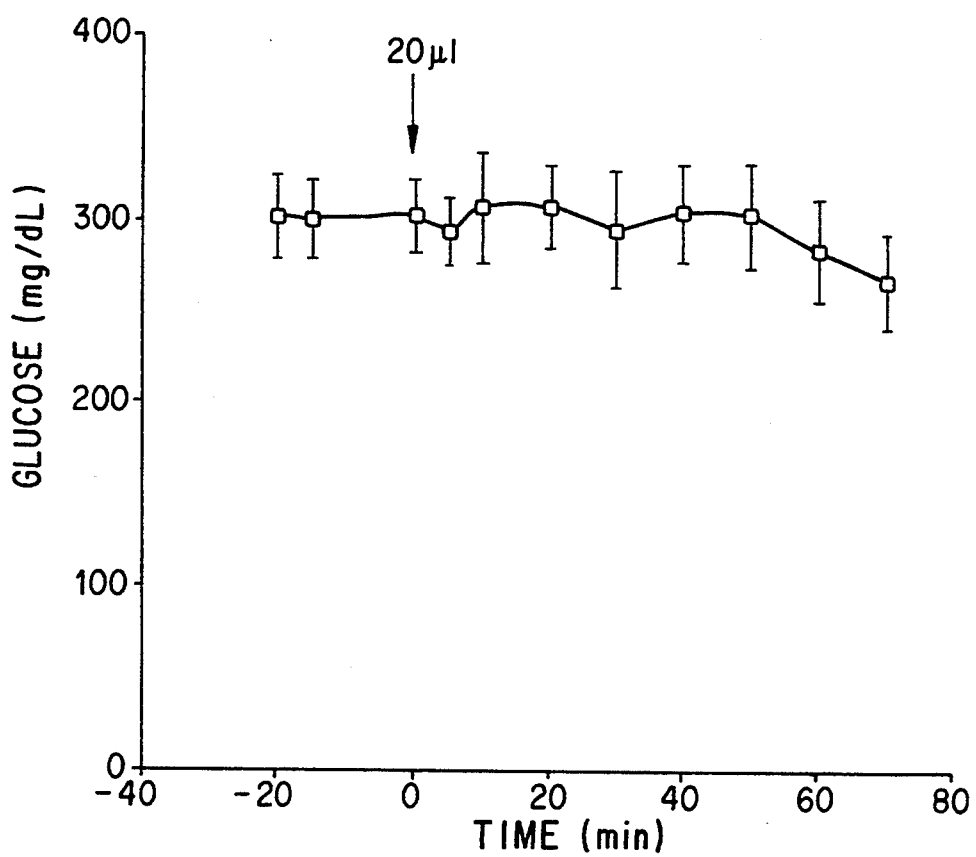
F I G. 4
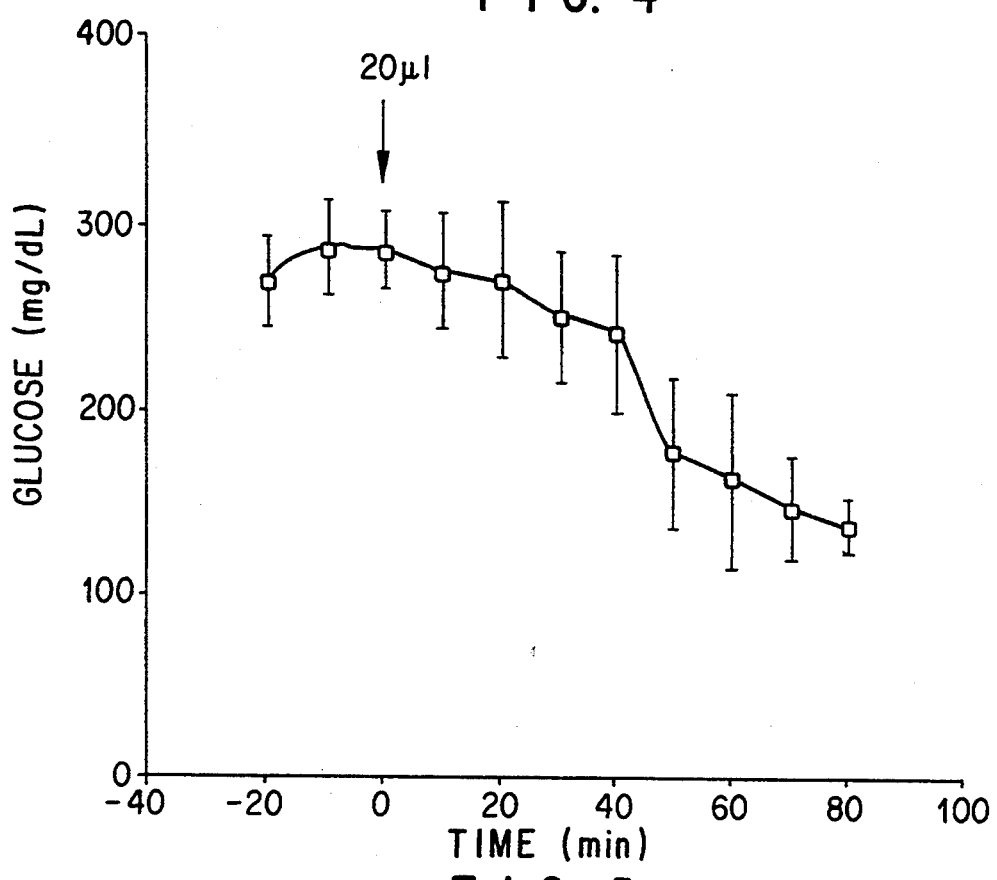
F I G. 5

MODIFIED SAPONINS ISOLATED FROM *QUILLAJA* SAPONARIA

CROSS-REFERENCE TO RELATED APPLICATION

This is a continuation-in-part of application Ser. No. 07/906,870 filed Jul. 2, 1992, now U.S. Pat. No. 5,273,965.

FIELD OF THE INVENTION

The present invention is in the field medicinal chemistry. In particular, the invention relates to modified saponins for enhancing drug delivery across mucosal membranes of an animal. The modified saponins of the present invention exhibit significantly reduced irritation to mucosal membranes compared to the natural saponins.

BACKGROUND OF THE INVENTION

It is known that certain small peptides can be absorbed through the nasal mucosa as a "snuff" or directly from aqueous solution. Gordon, G. S. et al., *Proc. Natl. Acad. Sci. USA* 82:7419–7423 (1985). However, the efficacy of absorption is typically low and variable and therapeutically important peptides of larger molecular size, such as insulin, are not absorbed to any appreciable degree. Hirai et al., *Diabetes* 27:296–299 (1978).

A number of researchers have attempted to increase the delivery of polypeptides with detergents. For example, Gordon, G. S. et al., *Proc. Natl. Acad. Sci. USA* 82:7419–7423 (1985), report that the nasal absorption of insulin can be increased by hydrophobic bile salts.

Longenecker, J. P. et al., *J. Pharm. Sci.* 76:351–355 (1987), disclose that sodium taurodihydrofusidate is an effective increaser of mucosal permeation of drugs, in particular, insulin.

Morimoto, K. et al., *J. Pharm. Pharmacol.* 37:134–136 (1984), disclose that the nasal absorption of insulin and calcitonin can be increased with polyacrylic acid gel.

See also Moses, A. C. et al., *Diabetes* 32:1040–1047 (1983), who disclose the administration of insulin as part of an insulin-bile salt aerosol; and Aungst, B. J. et al., *J. Pharm. Exp. Ther.* 244:23–27 (1988), who compared the nasal, rectal, buccal, sublingual and intramuscular insulin efficacy and the effects of a bile salt absorption promoter.

Maitani, Y. et al., *Drug Design Del.* 1:65–70 (1986), disclose the intranasal administration of β-interferon with and without surfactants (non-ionic, anionic and amphoteric). When no surfactant was used, β-interferon was not absorbed in rabbits. Sodium glycocholate was the most effective in enhancing the absorption of interferon following nasal administration. However, the total absorption of β-interferon with sodium glycocholate was 2.2% of the total absorption by intravenous administration.

Other detergents that have been employed to increase the uptake of polypeptides by mucosal tissue include saponins. Saponins occur widely in plant species (over 400) and exhibit a range of biological properties, some of which are beneficial and some deleterious. When agitated in water, they form a soapy lather and it is this characteristic that gives the group its name. Other properties generally ascribed to saponins include, for example, hemolytic activity, cholesterol-binding properties and bitterness. For a review of the chemistry and a biological significance of saponins, reference is made to Price, K. R. et al., *CRC Crit. Rev. Food Sci. Nutr.* 26:27 (1987).

Solutions of saponin have been employed to increase the delivery of polypeptides across mucosal membranes. For example, Pillion, D. J. et al., *Invest. Opthal. Vis. Sci.* 32:3021–27 (1991) disclose that administration of insulin in eyedrops containing unpurified saponin from Gypsophilla as a 1% solution causes a rapid and reproducible reduction in the blood levels of D-glucose in rats. Insulin eyedrops lacking saponin were ineffective. Japanese Abstract No. JP 62126135 (1987) discloses the nasal administration of growth hormone releasing factor employing a saponin having a steroidal or triterpene structure. See also, Chiou, G. C. Y. et al., *J. Pharm. Sci.* 78:815–818 (1989); and Chiou G. C. Y. et al., *J. Ocul. Pharm.* 5:81–91 (1989) who disclose the systemic delivery of insulin by administration as part of eyedrops containing saponin (obtained from Sigma Chemical Company). See also, Chiou, G. C. Y. et al., *Diabetes Care* 11:750–51 (1988) (source of saponin undisclosed). See also, Hirari, S. et al., *Int. J. Pharm.* 9:173–84 (1981) and Hirari, S. et al., *Int. J. Pharm.* 9:165–72 (1989), who disclose the nasal administration of insulin in rats with a solution comprising saponin (source not disclosed other than that the saponin was obtained from the Wako Pure Chemical Ind., Lid, Osaka, Japan).

While surfactants hold great promise for enhancing the uptake of drugs across mucosal membranes, a major drawback is that they cause irritation. Thus, the long-term use of pharmaceutical compositions comprising a surfactant cannot be possible. However, for acute therapies, local effects are less important because the mucosal membrane can easily repair itself. Long-term local toxicity effects are even more important when increasers are used to increase nasal membrane permeability. Chronic erosion of the mucous membrane by certain surfactants such as polyoxyethylene-9 lauryl ether could result in inflammation, hyperplasia, metaplasia and deterioration of normal nasal functions. Lee, W. A. and Longenecker, J. P., *BioPharm.* 30–37 (1988).

Literature reports indicate that biosalts break down mucous membrane structure (Martin, G. P. and Marriot, C., *J. Pharm. Pharmacol.* 31:754 (1981), accelerate phospholipid and protein release from membranes (Whitmore, D. A. et al., *J. Pharm. Pharmacol.* 31:277 (1979), and damage intestinal mucosa (Kimura, T. et al., *J. Nut. Sci. Vitaminol.* 28:483 (1982). Chronic erosion also exposes nasal circulation to a constant stream of airborne bacteria and related toxins. Lee, W. A. and Longenecker, J. P., *Biopharm.* 30–37 (1988). Thus, a need continues to exist for the development of new surfactants that increase the delivery of drugs across mucosal membranes without causing irritation.

SUMMARY OF THE INVENTION

The invention relates to a chemically modified saponin or a fraction thereof obtainable from a crude *Quillaja saponaria* extract, wherein the chemically modified saponin or fraction thereof comprises at least one of QA-17, QA-18, QA-21, QA-21-V1, and QA-21-V2, and wherein the chemical modification of the saponin or fraction thereof consists of
 (1) the reduction of the triterpene aldehyde group of QA-17, QA-18, QA-21, QA-21-V1, and QA-21-V2 to a methylenealcohol or a methyleneamino group; alone or in combination with (2) the hydrolysis of the fatty acid arabinose moiety or fatty acid arabinose-rhamnose moiety of QA-17, QA-18, QA-21, QA-21-V1, and QA-21-V2 to give the corresponding glycoside fragment.

The invention also relates to a pharmaceutical composition for increasing the uptake across mucous membranes of an animal of a pharmacologically active substance, comprising (a) chemically modified saponin or a fraction thereof obtainable from a crude Quillaja saponaria extract, wherein the chemically modified saponin or fraction thereof comprises at least one of QA-17, QA-18, QA-21, QA-21-V1, and QA-21-V2, and wherein the chemical modification of the saponin or fraction thereof consists of (1) the reduction of the triterpene aldehyde group of QA-17, QA-18, QA-21, QA-21-V1, and QA-21-V2 to a methylenealcohol or a methyleneamino group; or (2) the hydrolysis of the fatty acid arabinose moiety or fatty acid arabinose-rhamnose moiety of QA-17, QA-18, QA-21, QA-21-V1, and QA-21-V2 to give the corresponding glycoside fragment; or (3) a combination of (1) and (2);

(b) a pharmacologically active substance, and, optionally, (c) a pharmaceutically acceptable carrier.

The invention is also directed to a method for increasing the uptake of a pharmacologically active substance across a mucous membrane of an animal, comprising contacting said mucous membrane with a pharmaceutical composition, comprising (a) chemically modified saponin or a fraction thereof obtainable from a crude Quillaja saponaria extract, wherein the chemically modified saponin or fraction thereof comprises at least one of QA-17, QA-18, QA-21, QA-21-V1, and QA-21-V2, and wherein the chemical modification of the saponin or fraction thereof consists of (1) the reduction of the triterpene aldehyde group of QA-17, QA-18, QA-21, QA-21-V1, and QA-21-V2 to a methylenealcohol or a methyleneamino group; or (2) the hydrolysis of the fatty acid arabinose moiety or fatty acid arabinose-rhamnose moiety of QA-17, QA-18, QA-21, QA-21-V1, and QA-21-V2 to give the corresponding glycoside fragment; or (3) a combination of (1) and (2);

(b) a pharmacologically active substance, and, optionally, (c) a pharmaceutically acceptable carrier.

DESCRIPTION OF THE FIGURES

FIG. 4 shows the effect of the ocular administration of 0.1% QA-21-H (without insulin) on the blood glucose levels of rats.

FIG. 5 depicts the results of the ocular administration of 20 μl of 0.025% QA-21-H and 0.4% regular pork insulin on the mean of the blood glucose levels of three rats.

DESCRIPTION OF THE PREFERRED EMBODIMENTS

The present invention relates to the discovery that the irritation caused by saponins employed as part of a pharmaceutical composition to increase the delivery of pharmacologically active substances across mucosal membranes is reduced by modifying the aldehyde group of QA-17, QA-18, and QA-21, adjuvant compounds that are present in *Quillaja saponaria Molina* bark and that can be purified from this source.

The present invention employs modified saponins that have substantially no adjuvant activity or irritability when administered to an animal, but that retain sufficient lytic effect for drug transport. Such modified saponins can be obtained in several ways. For example, the aldehyde group of either purified QA-17, QA-18, QA-21, mixtures thereof, or purified fractions obtainable from *Quillaja saponaria Molina bark* and containing QA-17, QA-18, and QA-21 can be reduced with a mild reducing agent, such as sodium or lithium borohydride, to give the corresponding alcohol. See Scheme I. Alternatively, the aldehyde of QA-17, QA-18, and QA-21, mixtures thereof, or purified fractions obtainable from *Quillaja saponaria Molina bark* and containing QA-17, QA-18, and QA-21, can be subjected to reductive amination with a primary amine and a reducing agent to give the corresponding amino derivative of QA-17, QA-18, and/or QA-21. See Scheme II.

Examples of primary amines that can be used in the reductive alkylation procedure include, but are not limited to methylamine, ethylamine, propylamine, ethylenediamine, propylenediamine, 2-methyl-2-aminoethylamine, 3-methyl-3-aminopropylamine, 4-methyl-4-aminobutylamine, 5-methylaminopentylamine, 6-methylaminohexylamine, 3-methylamino-2-methylpropylamine, 2-ethylaminoethylamine, 3-ethylaminopropylamine, 4-ethylaminobutylamine, 5-ethylaminopentylamine, 6-ethylaminohexylamine, 3-propylaminopropylamine, 4-propylaminobutylamine, 5-propylaminopentylamine, 6-propylaminohexylamine, 2-(N,N'-dimethylamino)ethylamine, 3-dimethylaminopropylamine, 4-dimethylaminobutylamine, 5-dimethylaminopentylamine, 6-dimethylaminohexylamine, 3-dimethylamino-2-methylpropylamine, 2-(N,N'-diethylamino)ethylamine, 3-diethylaminopropylamine, 4-diethylaminobutylamine, 5-diethylaminopentylamine, 6-diethylaminohexylamine, 3-dipropylaminopropylamine, 4-dipropylaminobutylamine, 5-dipropylaminopentylamine, 6-dipropylaminohexylamine, 5-diethylaminopentan-2-amine and amino acids such as glycine, tyrosine, phenylalanine, methionine, alanine, serine, isoleucine, threonine, valine, proline, lysine, histidine, glutamine, glutamic acid, tryptophan, arginine, aspartic acid, asparagine or cysteine.

Scheme I

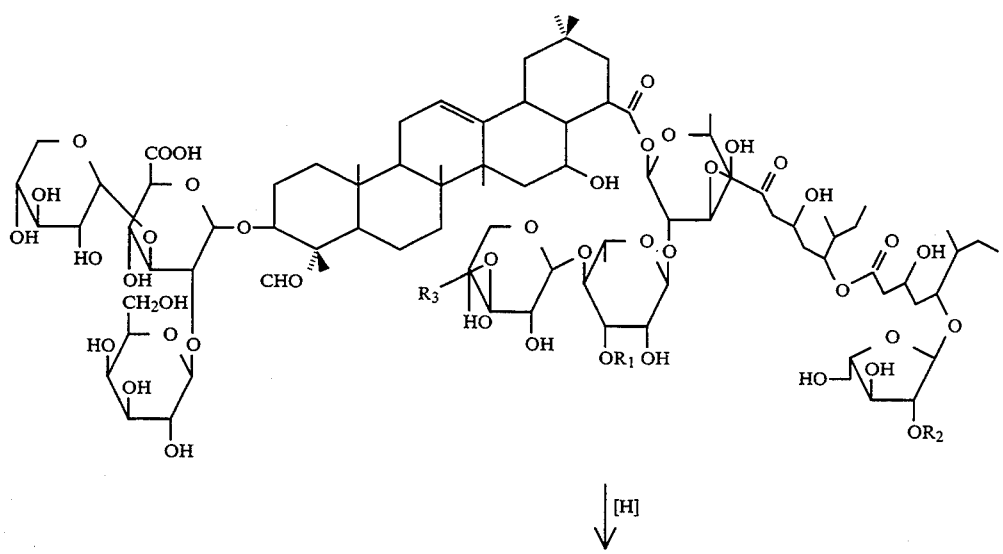

-continued
Scheme I

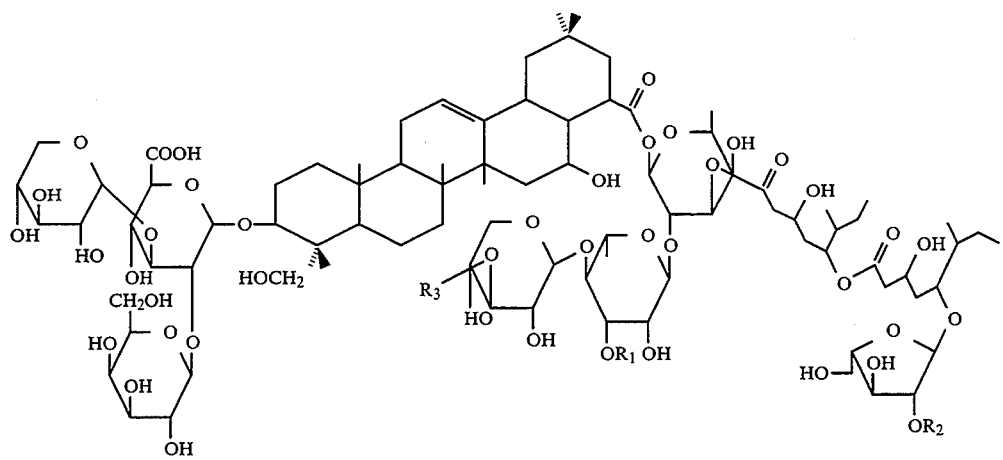

Scheme II

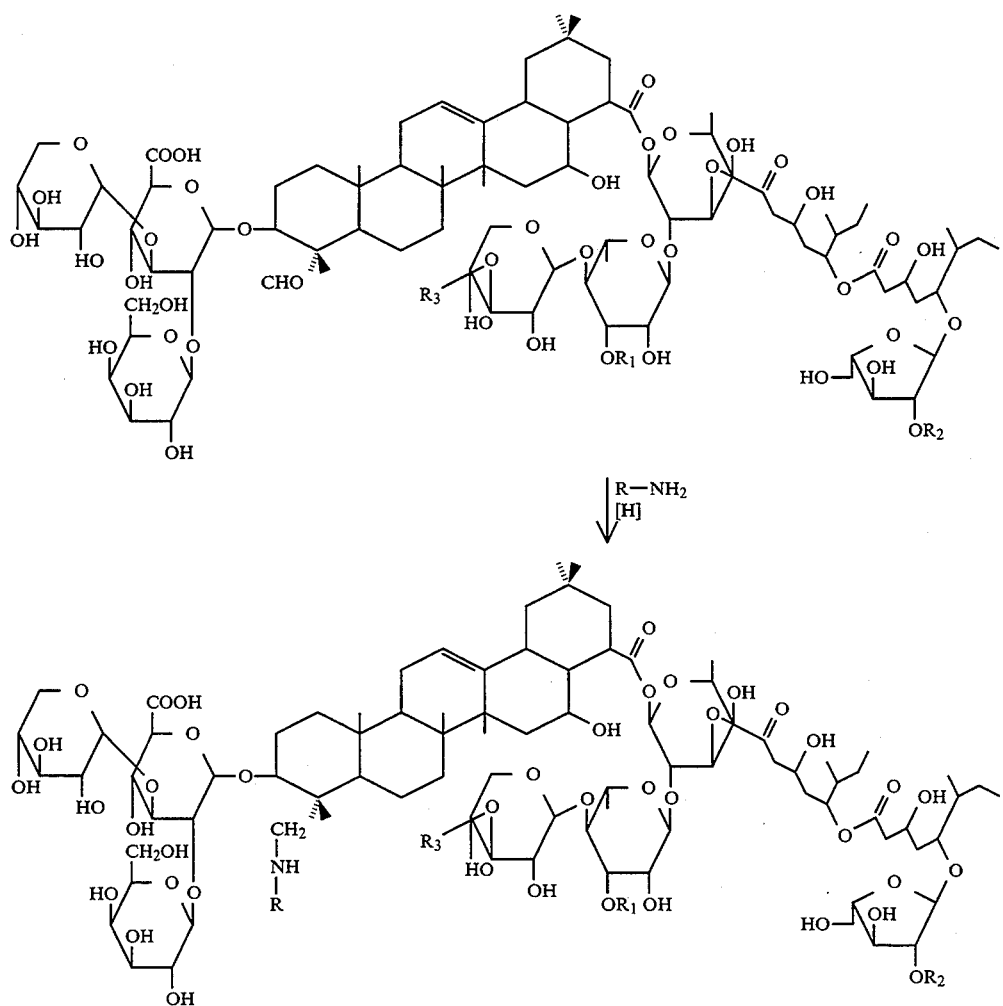

Figure 9A:
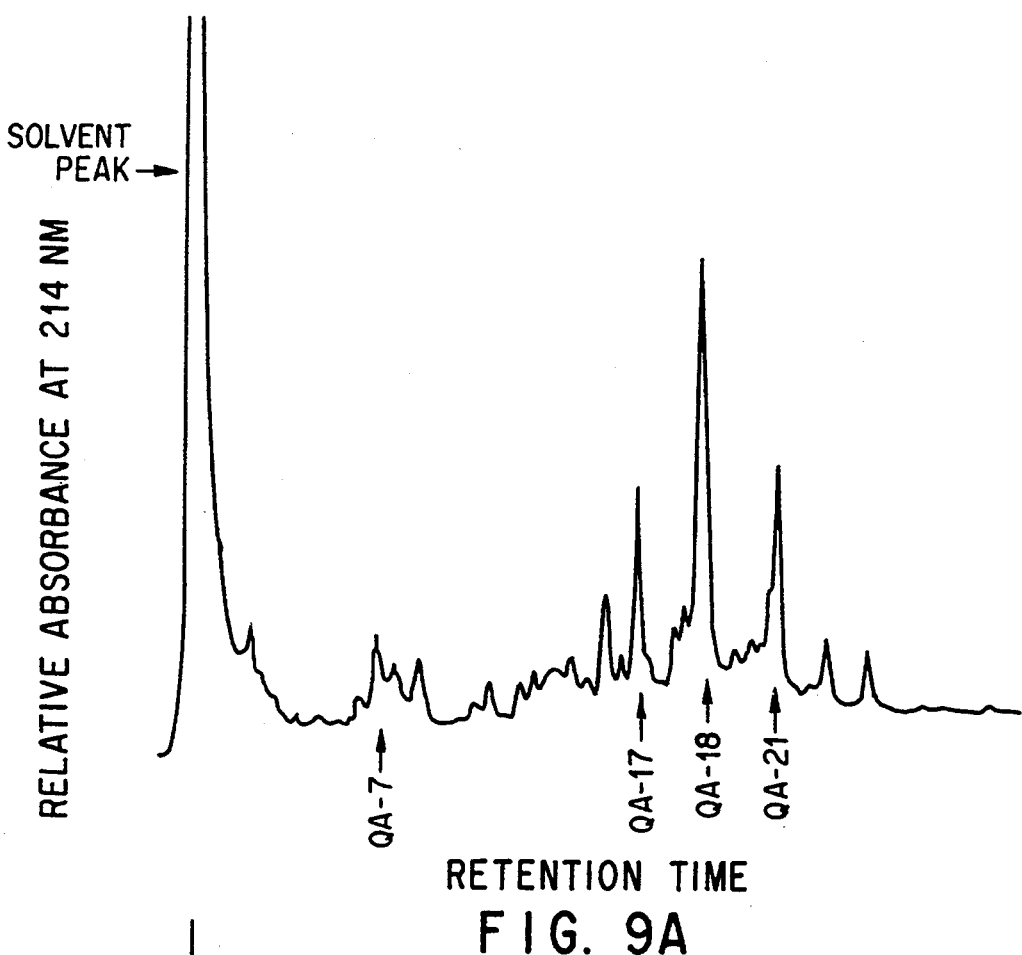
FIG. 9A depicts a reverse phase HPLC analysis of Quillaja saponaria bark extract.
Figure 9B:
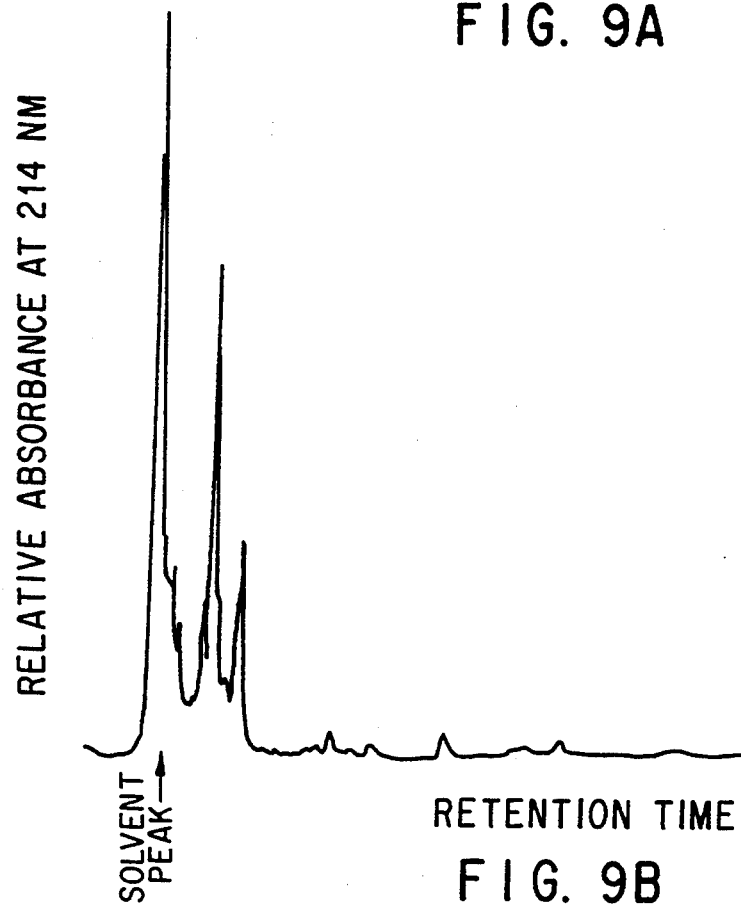
FIG. 9B depicts a reverse phase HPLC analysis of Quillaja saponaria bark extract after alkaline hydrolysis.
Figure 10A:
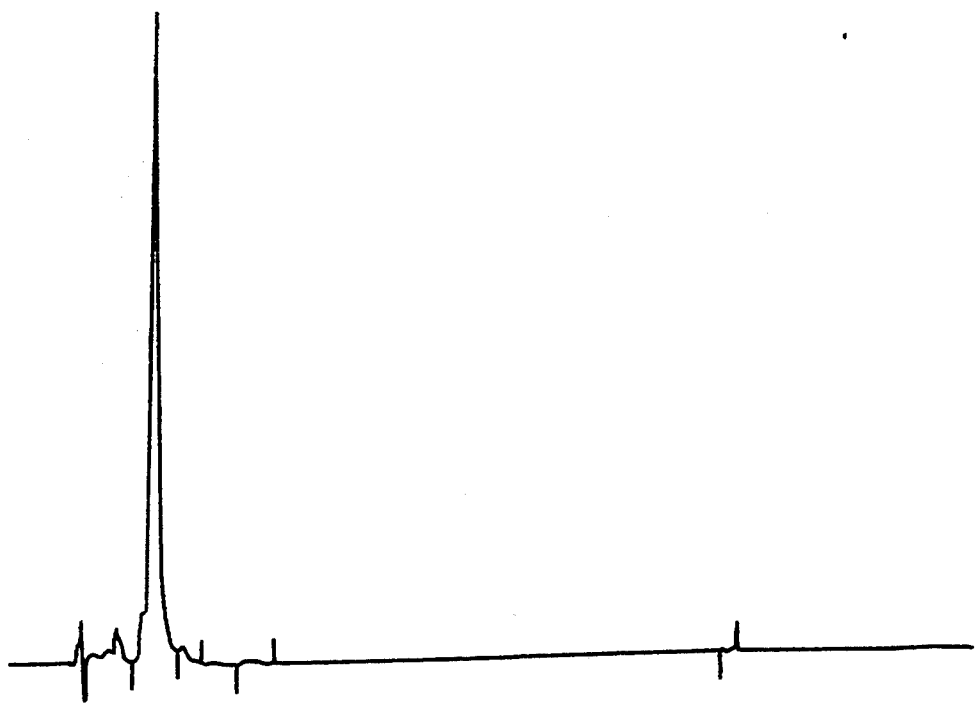
FIG. 10A depicts a reverse phase HPLC analysis of purified QA-18-H obtained from QA-18 after alkaline hydrolysis.
Figure 10B:
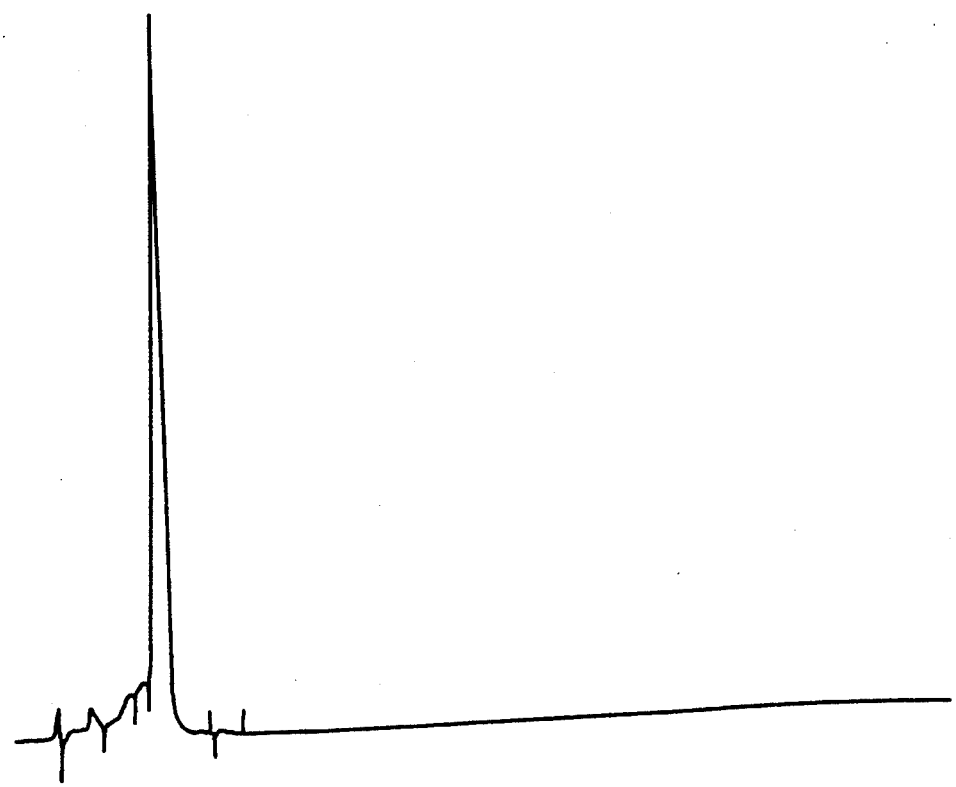
FIG. 10B depicts a reverse phase HPLC analysis of purified QA-21-H obtained from QA-21 after alkaline hydrolysis.

Preferably, a purified fraction of the saponin from *Quillaja saponaria* is employed, wherein the ester side chain has been hydrolyzed to decrease adjuvant activity. See Scheme III. The products of this hydrolysis, QA-18-H and QA-21-H, increase the uptake of drugs across mucosal membranes. Such hydrolysis can be carried out from purified saponins or can be carried out with a crude mixture, with subsequent purification of the modified saponins. FIG. 10 shows the reverse phase HPLC analysis of QA-18-H and QA-21-H obtained from purified QA-18 and QA-21, respectively. FIG. 9 shows that QA-18-H and QA-21-H are the predominant products and can be easily purified after alkaline hydrolysis of a crude extract from *Quillaja saponaria* bark.

sodium or lithium borohydride to give the corresponding methylenealcohol. Alternatively, the aldehyde group can be subjected to reductive amination with a

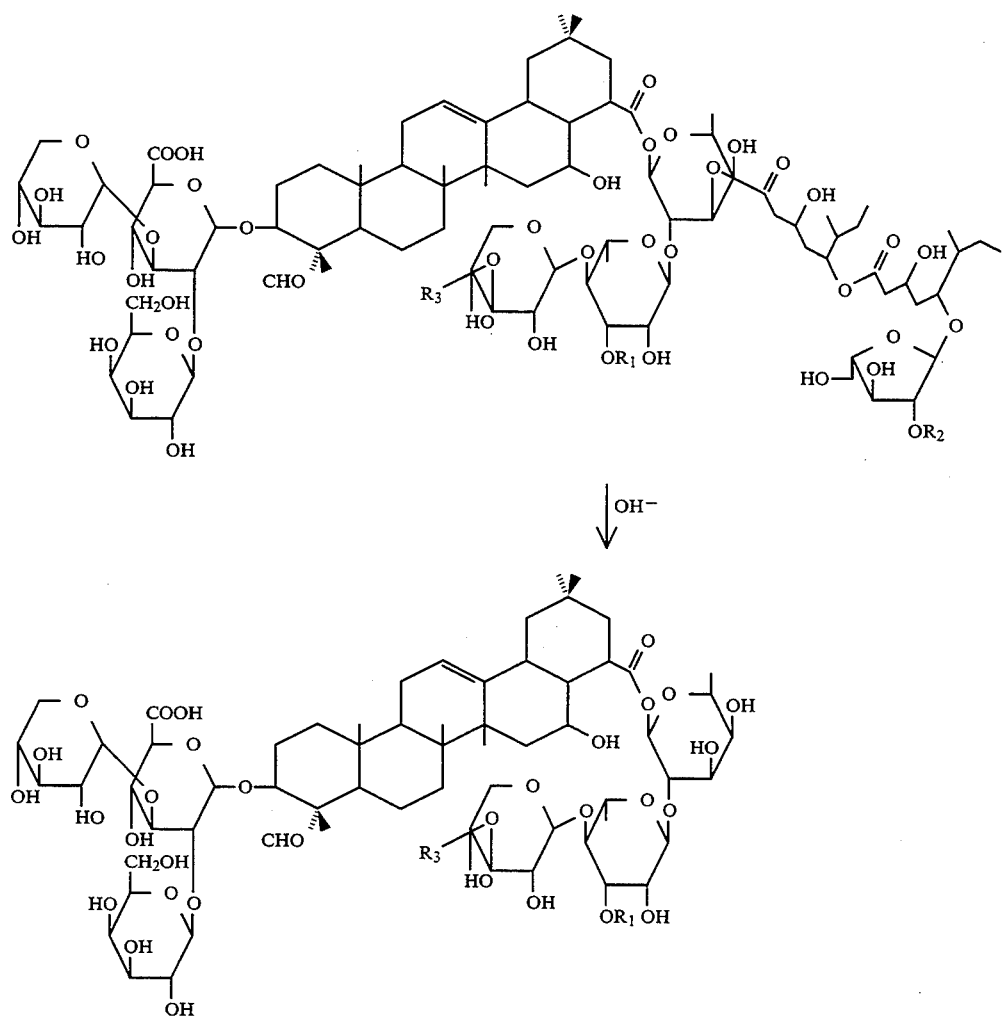

Preferably, QA-18-H and QA-21H are further modified to reduce the inflammatory response and residual adjuvant effect. As shown in Scheme IV, the aldehyde group of QA-18-H and QA-21-H can be reduced with primary amine and sodium or lithium borohydride to give the corresponding secondary amine. See Scheme IV.

Scheme IV

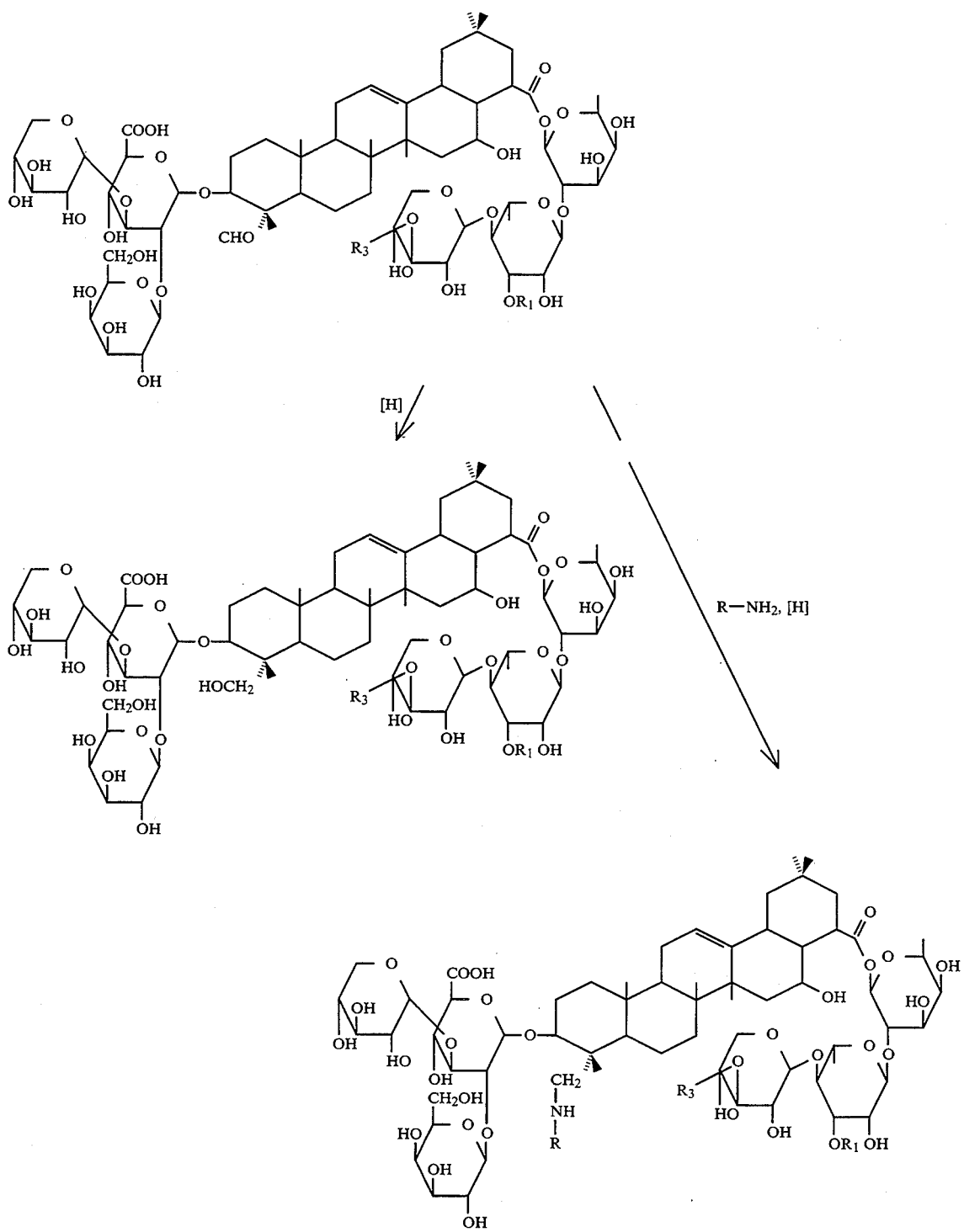

Thus, the present invention relates to a chemically modified saponin or a fraction thereof obtainable from a crude *Quillaja saponaria* extract, wherein the chemically modified saponin or fraction thereof comprises at least one of QA-17, QA-18, QA-21, QA-21-V1, and QA-21-V2, and wherein the chemical modification of the saponin or fraction thereof consists of
(1) the reduction of the triterpene aldehyde group of QA-17, QA-18, QA-21, QA-21-V1, and QA-21-V2 to a methylenealcohol or a methyleneamino group; alone or in combination with
(2) the hydrolysis of the fatty acid arabinose moiety or fatty acid arabinose-rhamnose moiety of QA-17, QA-18, QA-21, QA-21-V1, and QA-21-V2 to give the corresponding glycoside fragment.

The present invention also relates to a pharmaceutical composition for increasing the uptake across mucous membranes of an animal of a pharmacologically active substance, comprising (a) chemically modified saponin or a fraction thereof obtainable from a crude *Quillaja saponaria* extract, wherein the chemically modified saponin or fraction thereof comprises at least one of QA-17, QA-18, QA-21, QA-21-V1, and QA-21-V2, and wherein the chemical modification of the saponin or fraction thereof consists of (1) the reduction of the triterpene aldehyde group of QA-17, QA-18, QA-21, QA-21-V1, and QA-21-V2 to a methylenealcohol or a methyleneamino group; or (2) the hydrolysis of the fatty acid arabinose moiety or fatty acid arabinose-rhamnose moiety of QA-17, QA-18, QA-21, QA-21-V1, and QA-21-V2 to give the corresponding glycoside fragment; or (3) a combination of (1) and (2);

(b) a pharmacologically active substance; and, optionally, (c) a pharmaceutically acceptable carrier.

The amino groups have the formula $-N(R)-R'$, wherein R is hydrogen; R' is selected from the group consisting of hydrogen, $C_1-C_8$ alkyl, $C_2-C_{12}$ alkylaminoalkyl, allyl, aralkyl, $C_3-C_8$ cycloalkyl, aryl, and a group having the formula

wherein R" is hydrogen, $C_1-C_4$ alkyl, or $C_1-C_4$ alkyl substituted by phenyl, hydroxyphenyl, indolyl, mercapto, $C_1-C_4$ alkylthio, hydroxy, carboxy, amino, guanidino, imidazolyl or carbamyl; or wherein R and R" together form a pyrrolidinyl or piperidinyl ring.

Typical $C_1-C_8$ alkyl groups include methyl, ethyl, propyl, butyl, pentyl, hexyl, heptyl, and octyl groups and isomers thereof.

Typical $C_3-C_8$ cycloalkyl groups include cyclopropyl, cyclobutyl, cyclopentyl, cyclohexyl, cycloheptyl, and cyclooctyl groups.

Typical aryl groups include phenyl, naphthyl, phenanthryl, anthracyl and fluorenyl groups.

Typical aralkyl groups include a $C_1-C_8$ alkyl group substituted by one of the above-listed aryl groups, e.g. phenethyl, phenylpropyl, phenylbutyl, phenylpentyl, and phenylhexyl groups, as well as the branched chain isomers thereof.

Typical $C_2-C_{12}$ alkylaminoalkyl groups include 2-methylaminoethyl, 3-methylaminopropyl, 4-methylaminobutyl, 5-methylaminopentyl, 6-methylaminohexyl, 3-methylamino-2-methylpropyl, 2-ethylaminoethyl, 3-ethylaminopropyl, 4-ethylaminobutyl, 5-ethylaminopentyl, 6-ethylaminohexyl, 3-propylaminopropyl, 4-propylaminobutyl, 5-propylaminopentyl, 6-propylaminohexyl, 2-(N,N'-dimethylamino)ethyl, 3-dimethylaminopropyl, 4-dimethylaminobutyl, 5-dimethylaminopentyl, 6-dimethylaminohexyl, 3-dimethylamino-2-methylpropyl, 2-(N,N'-diethylamino)ethyl, 3-diethylaminopropyl, 4-diethylaminobutyl, 5-diethylaminopentyl, 6-diethylaminohexyl, 3-dipropylaminopropyl, 4-dipropylaminobutyl, 5-dipropylaminopentyl, 6-dipropylaminohexyl, 5-diethylaminopentan-2-yl and the like.

According to U.S. Pat. No. 5,057,540, the contents of which are fully incorporated by reference herein, saponins can be purified from an aqueous extract of the bark of the South American tree, *Quillaja saponaria Molina*. At least 22 peaks with saponin activity were separable. The predominant purified Quillaja saponins are QA-7, QA-17, QA-18, and QA-21. These saponins have been purified by high pressure liquid chromatography (HPLC) and low pressure silica chromatography. QA-21 can be further purified using hydrophilic interaction chromatography (HILIC) and resolved into two peaks, QA-21-V1 and QA-21-V2, that are different compounds. Thus, "QA-21" designates the mixture of components QA-21-V1 and QA-21-V2 that appear as a single peak on reverse phase HPLC on Vydac C4 (5 μm particle size, 330 Å pore, 4.6 mm ID×25 cm L) in 40 mM acetic acid in methanol/water (58/42, v/v). The component fractions are referred to specifically as QA-21-V1 and QA-21-V2 when describing experiments or results performed on the further purified components.

In order to purify saponins from *Quillaja saponaria Molina* bark, aqueous extracts of the *Quillaja saponaria Molina* bark are dialyzed against water. The dialyzed extract is lyophilized to dryness, extracted with methanol and the methanol-soluble extract is further fractionated by silica gel chromatography and by reverse phase high pressure liquid chromatography (RP-HPLC). The individual saponins are separated by reverse phase HPLC. At least 22 peaks (designated QA-1 to QA-22) are separable. Each peak corresponds to a carbohydrate peak that exhibits only a single band on reverse phase thin layer chromatography. The individual components were identified by retention time on a Vydac C4 HPLC column as follows:

| Peak | Retention Time (minutes) |
| --- | --- |
| QA-1 | solvent front |
| QA-2 | 4.6 |
| QA-3 | 5.6 |
| QA-4 | 6.4 |
| QA-5 | 7.2 |
| QA-6 | 9.2 |
| QA-7 | 9.6 |
| QA-8 | 10.6 |
| QA-9 | 13.0 |
| QA-10 | 17.2 |
| QA-11 | 19.0 |
| QA-12 | 21.2 |
| QA-13 | 22.6 |
| QA-14 | 24.0 |
| QA-15 | 25.6 |
| QA-16 | 28.6 |
| QA-17 | 35.2 |
| QA-18 | 38.2 |
| QA-19 | 43.6 |
| QA-20 | 47.6 |
| QA-21 | 51.6 |
| QA-22 | 61.0 |

The substantially pure QA-17 saponin is characterized as having adjuvant activity, containing about 29% carbohydrate (as assayed by anthrone) per dry weight, having a UV absorption maximum of 205-210 nm, a retention time of approximately 35 minutes on RP-HPLC on a Vydac C4 column having 5 μm particle size, 330 Å pore, 4.6 mm ID×25 cm L in a solvent of 40 mM acetic acid in methanol-water (58/42; v/v) at a flow rate of 1 ml/min, eluting with 63-64% methanol from a Vydac C4 column having 5 μm particle size, 300 Å pore, 10 mm ID×25 cm L in a solvent of 40 mM acetic acid with gradient elution from 50 to 80% methanol, having a critical micellar concentration of 0.06% (w/v)

in water and 0.03% (w/v) in phosphate buffered saline, causing hemolysis of sheep red blood cells at 25 μg/ml or greater, and containing the monosaccharide residues terminal rhamnose, terminal xylose, 2-fucose, 3-xylose, 3,4-rhamnose, 2,3-glucuronic acid, terminal glucose, 2-arabinose, terminal galactose and apiose (linkage not determined).

The substantially pure QA-18 saponin is characterized as having immune adjuvant activity, containing about 25–26% carbohydrate (as assayed by anthrone) per dry weight, having a UV absorption maximum of 205–210 nm, a retention time of approximately 38 minutes on RP-HPLC on a Vydac C$_4$ column having 5 μm particle size, 330 Å pore, 4.6 mm ID×25 cm L in a solvent of 40 mM acetic acid in methanol/water (58/42; v/v) at a flow rate of 1 ml/min, eluting with 64–65% methanol from a Vydac C$_4$ column having 5 μm particle size, 330 Å pore, 10 mm ID×25 cm L in a solvent of 40 mM acetic acid with gradient elution from 50 to 80% methanol, having a critical micellar concentration of 0.04% (w/v) in water and 0.02% (w/v) in phosphate buffered saline, causing hemolysis of sheep red blood cells at concentrations of 25 μg/ml or greater, and containing the monosaccharides terminal arabinose, terminal apiose, terminal xylose, terminal glucose, terminal galactose, 2-fucose, 3-xylose, 3,4-rhamnose, and 2,3-glucuronic acid.

The substantially pure QA-21 saponin is characterized as having immune adjuvant activity, containing about 22% carbohydrate (as assayed by anthrone) per dry weight, having a UV absorption maximum of 205–210 nm, a retention time of approximately 51 minutes on RP-HPLC on a Vydac C$_4$ column having 5 μm particle size, 330 Å pore, 4.6 mm ID×25 cm L in a solvent of 40 mM acetic acid in methanol/water (58/42; v/v) at a flow rate of 1 ml/min, eluting with 69 to 70% methanol from a Vydac C$_4$ column having 5 μm particle size, 330 Å pore, 10 mm×ID 25 cm L in a solvent of 40 mM acetic acid with gradient elution from 50 to 80% methanol, with a critical micellar concentration of about 0.03% (w/v) in water and 0.02% (w/v) in phosphate buffered saline, and causing hemolysis of sheep red blood cells at concentrations of 25 μg/ml or greater. The component fractions, substantially pure QA-21-V1 and QA-21-V2 saponins, have the same molecular weight and identical spectra by fast atom bombardment—mass spectroscopy (FAB-MS). They differ only in that QA-21-V1 has a terminal apiose that is xylose in QA-21-V2 (which therefore has two terminal xyloses and no apiose). The two components additionally contain the monosaccharides terminal arabinose, terminal apiose, terminal xylose, 4-rhamnose, terminal galactose, 2-fucose, 3-xylose, and 2,3-glucuronic acid.

The alkaline hydrolysis products can be prepared as follows. Treatment of QA-18 by brief alkaline hydrolysis yielded one major carbohydrate-containing alkaline hydrolysis product (designated QA-18-H). Purified QA-18-H was prepared from QA-18 and isolated in the following manner:

One ml QA-18 (5 mg/ml) was incubated with 25 μl 1N NaOH for 15 minutes at room temperature. The reaction was stopped with the addition of 100 μl 1N acetic acid. Using these hydrolysis conditions, QA-18 was completely converted to a major hydrolysis product (QA-18-H) eluting in a peak with retention time of 8.0 min compared to 66.8 min for unhydrolyzed QA-18, indicating the increased hydrophilicity of QA-18-H. (Chromatography on Vydac C$_4$ (4.6 mm ID×25 cm L)

in 0.1% trifluoroacetic acid in 55/45 methanol/water (v/v) and eluted in a gradient to 64/36 methanol/water (v/v) over 180 minutes, flow rate of 1 ml/minute). The peak containing pure QA-18-H (retention time 8.0 min) was pooled for further characterization. The hydrolysis product of QA-21, designated QA-21-H, was prepared and purified in the same manner. QA-21-H had a retention time of 9.3 minutes compared to 80.4 minutes for unhydrolyzed QA-21. These hydrolysis products were shown by retention time on HPLC and by reverse phase thin layer chromatography to be identical to the major hydrolysis products generated using the method of Higuchi et al., *Phytochemistry* 26:229 (1987) using mild alkaline hydrolysis in NH$_4$HCO$_3$ (Table 1). In addition, these products, QA-18-H and QA-21-H, were shown to be the major breakdown products from hydrolysis of "Quil-A", a crude saponin mixture containing QA-7, QA-17, QA-18, and QA-21 as well as other saponins, indicating that the hydrolysis products QA-21-H and QA-18-H are the same hydrolysis products isolated by Higuchi et al., supra, for structural characterization.

TABLE 1

| Retention Time of Major Alkaline Hydrolysis Products | |
|---|---|
| QA-17-H | 8.0$^a$ |
| QA-18-H | 8.0$^a$ |
|  | 8.2$^b$ |
| QA-21-H | 9.3$^a$ |
|  | 9.5$^b$ |
| Hydrolyzed - "Quil-A" | 8.2$^a$, 9.3$^a$ |

$^a$Cambridge BioScience hydrolysis conditions: 5 mg/ml saponin, pH 13, reaction time = 15 minutes at room temperature
$^b$Higuchi et al. hydrolysis conditions: 5 mg/ml saponin, 6% NH$_4$HCO$_3$, methanol/H$_2$O (1/1, v/v), reaction time = 60 minutes at 100° C.

HPLC Conditions:
  Vydac C$_4$, 5 μm particle size, 300 Å pore size, 0.46×25 cm
  Solvent A=0.1% trifluoroacetic acid in water
  Solvent B—0.1% trifluoroacetic acid in methanol
  Gradient=55–64% B/180 minutes
  Flow rate—1 ml/min The compositions of the invention comprising the modified saponins can be employed to increase the uptake across mucosal membranes of any one of a large number of pharmacologically active substances. Preferably, such pharmacologically active substances are polypeptides. However, the invention is not intended to be so limited. The compositions comprising the modified saponins of the invention can be used to increase the uptake of any pharmacologically active substance, so long as its molecular weight is less than about 200,000 daltons.

Examples of such polypeptides that can be administered together with the compositions of the present invention include, but are not limited to, insulin, insulin-like growth factor, growth hormone, parathyroid hormone, renin, prolactin, thyroid stimulating hormone, corticotropin, follicle stimulating hormone, chorionic gonadotropin, luteinizing hormone, luteinizing releasing factor, interferon (alpha, beta, and gamma), lymphokines, interleukin, tumor necrosis factor, antibodies (monoclonal and polyclonal), e.g. IgG, enkephalins (see Su, K. S. E., et al., *J. Pharm. Sci.* 74:394–98 (1985)), calcitonin (McMartin, C. and Peters, G., *Delivery Systems For Peptide Drugs*, S. S. Davis et al. (eds.), pp. 249–53, Planum Press New York (1986)), somatostatin (McMartin, C. and Peters, G., *Delivery Systems For Peptide Drugs*, Davis, S. S., et al. (eds.), pp. 255–63, Planum Press New York (1986)), methionyl growth hormone (Moore, J. A. et al., *Delivery Systems For Peptide Drugs*, Davis, S. S., et al. (eds.), pp. 317–329, Planum Press New York (1986)), oxytocin (Hendricks, C. H. and Pose, S. V., *J.A.M.A.* 175:384–387 (1961)), vasopressin and desmopressin (Richson, D. W. and Robinson, A. G., *Ann. Int. Med.* 103:228–239 (1985)), luteinizing hormone releasing hormone (Fink, G. et al., *J. Endocr.* 63:351–360 (1974)), nafarelin acetate (Anik, S. T. et al., *J. Pharm. Sci.* 73:684–685 (1984)), secretin (Ohwaki, T. et al., *J. Pharm. Sci.* 74(5):550–552 (May, 1985)), glucagon (Pontiroli, A. E. et al., *Acta Diabetol Let.* 22:102–110 (1985)), pimolol (Kaila, T. et al., *J. Ocular Pharm.* 1:79–83 (1985), thyrotropin-releasing hormone (Sandow, J. and Petri, W., *Trans Nas. System. Med.*, (Chien, Y. W. ed.) Elsevier Science Publishers B. B., Amsterdam, pp. 183–199 (1985)).

In addition, the compositions of the present invention can also be employed to increase the uptake across mucosal membranes of enzymes, transferases, hydrolases, isomerases, proteases, ligases and oxidoreductases such as esterases, phosphatases, glycosidases and peptidases; enzyme inhibitors such as leupeptin, chymostatin and pepstatin and growth factors, such as tumor angiogenesis factor.

Other suitable pharmacologically active substances are fat-soluble steroids such as progesterone, estrogens and androgens, as well as the fat soluble vitamins A, D, E and K.

In addition to low and high molecular weight polypeptides, the pharmacologically active substance can be an anti-inflammatory agent (e.g., indomethacin, flurbiprofen, ketoprofen, ibuprofen, phenylbutazone), antibiotics (e.g., beta-lactams, aminoglycosides, macrolides, tetracyclines, pryridonecarboxylic acids, phosphomycin), anti-tumor agents (e.g., adriamycin, cisplatin, bleomycin, mitomycin, fluorouracil, vinblastine, vincristine), amino acids (e.g., ascorbic acid, N-acetyltryptophan), antifungal agents, prostaglandins, vitamins, steroids, vaccine antigens, vaccine adjuvants and antiviral agents (AZT, DDI, acyclovir, idoxuridine, amantadine, and vidarabine).

The compositions of the present invention can be applied to any mucous membrane including the conjunctiva, nasopharynx, orthopharnyx, vagina, colon, urethra, urinary bladder, lung, large (rectal) and small (enteral) intestine. The compositions of the present invention can also be administered transdermally, for example, as part of a patch. Preferably, the compositions of the present invention are administered to the eye as part of eye drops, nasally as part of an aerosol or buccally as part of a solid wafer. In addition, the pharmaceutical compositions of the present invention can also be formulated in sustained release compositions. For example, the modified saponin and drug can be combined with a silicone elastomer that releases the saponin and drug over a long period of time. The silicone elastomer can also comprise albumin. See U.S. Pat. No. 4,985,253, the contents of which are fully incorporated by reference herein. The release rate of the drug from the silicone elastomer can be controlled by incorporation of a water soluble or fat soluble mixing agent or cosolvent (e.g., polyethylene glycol 400, polysorbate 80, sodium alginate, L-alanine, sodium chloride, polydimethylsiloxane) into the silicone elastomer. Any other additive can also be incorporated into the silicone elastomer for the purpose of accelerating the release rate.

In addition, the pharmacologically active substance and saponin can be formulated in a controlled release composition comprising a polylactide and/or polyglycolide copolymer, a cellulose polymer (methyl-, methylhydroxyethyl-, hydroxypropyl-, hydroxyethyl-, sodium carboxyethyl-cellulose), polyacrylic acid, polymethylmethacrylate, cross-linked polyacrylic acid, polyvinylpyrrolidone, polyvinylalcohol, polyethylene glycol, agarose or a copolymer of styrene and hydroxyethylmethacylate crosslinked with divinylazobenzene. Alternatively, the pharmacologically active substance and saponin can be formulated as part of DEAE-dextran microspheres, starch microspheres, or albumin microspheres.

When the saponin and pharmacologically active substance are formulated in a sustained release composition, the content of the pharmaceutical substance can be appropriately controlled depending upon the dose to be administered and the release rate. When the composition is shaped in matrix type preparation, the content of the pharmaceutical substance can usually be from 5 to 40% by weight and, more preferably, not more than 15% by weight, for example, 9% by weight or less. When administering a peptide hormone, its content should be no more than about 6 to 10% by weight. Albumin, if employed, is present at not more than 50% by weight, preferably from about 20 to 30% by weight. The silicone elastomer can be contained in an amount of not less than 50% by weight, preferably from 70 to 90% by weight.

The sustained release compositions can be prepared by mixing the components in any optional order. When albumin is added, the drug and albumin are first combined, preferably in a solid state. Alternatively, an aqueous solution of the pharmaceutical substance and albumin can be mixed and the resulting mixture lyophilized to make a solid mixture. This mixture is then dispersed uniformly with an elastomer base, optionally, with a plasticizer (e.g., dimethypolysiloxane), adding a curing agent thereto and stirring the resultant mixture. The mixture is then placed in an appropriate mold and cured at room temperature to give a shaped composition. In the alternative, a core material not containing a pharmaceutical substance can be covered with the composition comprising a silicone elastomer containing a pharmaceutical substance, optionally containing albumin, to make a shaped composition. Such core material can comprise any non-toxic material. Preferably, such core material is an elastic polymer.

The sustained release compositions of the present invention can have any shape that is suitable for effective contact with mucous membranes in body cavities. For example, when the pharmacologically active substance is administered buccally, the sustained release composition can be in the form of a wafer. When the pharmacologically active substance is administered vaginally, the sustained release composition can be in the form of a ring. When administered ocularly, the sustained release composition can be in the form of thin ocular implants.

The compositions of the present invention can also be formulated as part of a chewing gum comprising the gum from the latex of the sapodilla. Preferably, the chewing gum composition also comprises sweeteners (sugar, aspartame and the like) and flavorants (spearmint, wintergreen or peppermint oil and the like) that masks any unpleasant taste associated with the pharmacologically active substance.

When administered ocularly or nasally, the compositions of the present invention can be formulated in an aqueous solution buffered to a pH of between 3.0 and 8.0, most preferably pH 5.0–5.4, by means of a pharmaceutically acceptable buffer system. Any pharmaceutically acceptable buffering system capable of maintaining the pH in the preferred ranges can be used in the practice of this invention. A typical buffer will be, for example, an acetate buffer, a phosphate buffer, a citrate buffer, a succinate buffer or the like. The concentrate of buffer can range from between 0.005 and 0.1 molar, most preferably about 0.02 molar.

When the compositions of the present invention are administered ocularly, the composition can comprise a solution containing sodium, potassium, magnesium, calcium, chloride and bicarbonate ions as well as dextrose and glutathione. See, for example, U.S. Pat. Nos. 4,550,022, 4,443,432. Alternatively, the ocular fluid can comprise an aqueous solution containing sodium chloride, potassium chloride, calcium chloride and N-2-hydroxyethylpiperazine-N-2-ethanesulphonic acid. Sodium hydroxide can be included to establish a pH value of about 7.25 and magnesium sulfate can also be included. See UK Patent Application GB 2,064,320. See also U.S. Pat. No. 4,938,970, which discloses irrigation solutions that do not cause pain when administered to the eye. According to this patent, the electrolyte solution comprises 2–10 meq/L of $K^+$, 0–3 meq/L of $Ca^{++}$, 1–5 meq/L of $Mg^{++}$ and 110–150 meq/L of $Na^+$, buffered to a pH of 6.85–8.0.

Other materials, such as preservatives, salts to achieve the tonic value of tissue, or other additives indicated by known nasal or ocular formulation chemistry, can be added to these formulations.

By the term "animal" is intended all animals that might derive a benefit from the compositions of this invention. Foremost among such animals are humans; however, the invention is not intended to be so limited, it being within the contemplation of the invention to treat any and all such animals that can experience the beneficial effects of the present invention.

For nasal administration, the compositions of the invention will preferably be in a container provided with means for enabling application of the contained composition to the nasal mucosa, e.g., with a nasal applicator device. Suitable applicators are known in the art and include those adapted for administration of liquid compositions to the nasal mucosa in drop or spray form. Since dosing with polypeptides should be as accurately controlled as possible, the use of spray applicators for which the administered quantity is susceptible to precise regulation are generally preferred. Suitable administrators include e.g., atmosing devices, e.g., pop-atomizers and aerosol dispensers. In the latter case, the applicator will contain the composition of the present invention together with a propellant medium suitable for use in a nasal applicator. The atomizing device will be provided with an appropriate spray adaptor allowing delivery of the contained composition to the nasal mucosa. Such devices are well known in the art.

The container, e.g. nasal applicator or eye drop bottle, can contain sufficient composition for a single nasal or ocular dosing or for supply of several sequential dosages, e.g. over a period of days or weeks.

The following examples are illustrative, but not limiting of the method and compositions of the present invention. Other suitable modifications and adaptations of the variety of conditions and parameters normally encountered in clinical therapy and that are obvious to those skilled in the art are within the spirit and scope of the present invention.

EXAMPLE 1

Conjugation of Glycine and Ethylenediamine to QA-21 Triterpene Aldehyde Via Reductive Alkylation To react glycine with the QA-21 triterpene aldehyde, 20 mg of QA-21 was dissolved in 0.8 ml of 50% methanol, 50 mM sodium phosphate, pH 6.0. A 0.5 ml solution of glycine was prepared in water. A total of 0.1 ml of glycine was added to the QA-21 solution. A 0.1M solution of sodium cyanoborohydride was prepared in methanol (32 mg in 5 ml). A total of 0.1 ml of the sodium cyanoborohydride was added to the QA-21 solution. The addition of sodium cyanoborohydride was repeated at 2.5; 21, 25, and 46 hours. The reaction mixture was purified by reverse phase HPLC. A new peak at 31.3 minutes was collected. The new product was confirmed by FAB-MS To react ethylenediamine with the QA-21 triterpene aldehyde, 6 mg of QA-21 was dissolved in 1 ml 50% methanol, 20 mM triethylamine phosphate, pH 6. A total of 0.15 ml of a 0.1M ethylenediamine solution in water was added, followed by 0.06 ml of 50 mM sodium cyanoborohydride in methanol. Additional aliquots of the sodium cyanoborohydride were added at 45 minutes and 16 hours. The reaction was purified by reverse phase HPLC on a 30–60% B method. A new peak at 19.6 minutes was collected. This material was freeze-dried. The resulting peak was analyzed by reverse phase thin layer chromatography and shown to be reactive with ninhydrin, indicating the addition of a free amino group to QA-21.

EXAMPLE 2

Reduction of the QA-21 Triterpene Aldehyde to Methylenealcohol

Twelve mg of QA-21 in four ml of water was mixed with 8 ml of 0.1M sodium phosphate, pH 6.0 for a final QA-21 concentration of 1 mg/ml. A stock solution of 1M sodium borohydride was prepared in 0.01M NaOH. A total volume of 0.580 ml of sodium borohydride was added to the QA-21 in small increments (approximately 50 μl increments). The final concentration of sodium borohydride was 0.05M. This reaction mixture was incubated for one hour at room temperature. The reaction was quenched with 1 ml of 1N acetic acid. To remove sodium borohydride, the QA-21 was adsorbed to $C_{18}$. Four mls of reaction mixture was passed through a cartridge containing $C_{18}$. The cartridge was then washed with two 5 ml water washes. The QA-21 was then eluted from the $C_{18}$ with 5 ml of methanol. This process was repeated with the remaining 8 ml of reaction mixture. The methanol was evaporated under a stream of $N_2$. The reduced QA-21 was then redissolved in 30% acetonitrile/0.15% trifluoroacetic acid and purified by HPLC to remove residual unreduced QA-21 (Vydac $C_4$, 5 μm particle size, in a gradient of 25–40% B over 60 minutes at a flow rate of 3 ml/min (Solvent A—0.15% trifluoroacetic acid (TFA) in water, Solvent B—0.15% TFA in acetonitrile)). The reduced QA-21 eluted with a retention time of 46.8 minutes (compared to a retention time of 48.1 minutes for unreduced QA-21). The peak corresponding to the reduced QA-21 was pooled, diluted ½ with water and collected on $C_{18}$ cartridges as described above. The final product was lyophilized and used for immunization studies.

EXAMPLE 3

Adjuvant Activities of Modified QA-21 Saponins

Figure 11:
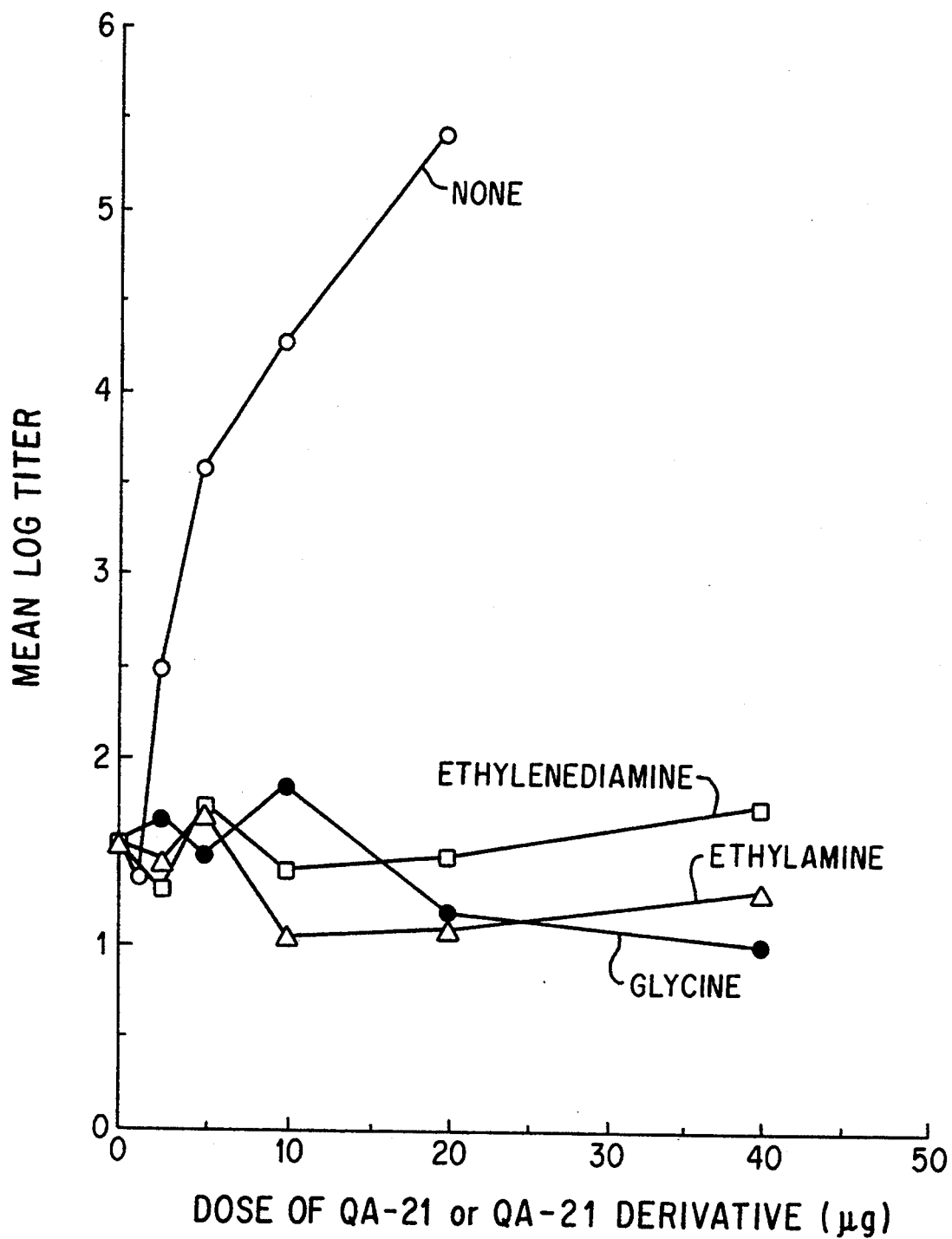
FIG. 11 depicts a graph showing the adjuvant activities of QA-21 (○), QA-21 modified at the triterpene aldehyde by reductive amination with glycine ( ), QA-21 modified at the triterpene aldehyde by reductive amination with ethylenediamine (□), and QA-21 modified at the triterpene aldehyde by reductive amination with ethylamine (Δ).
Figure 12:
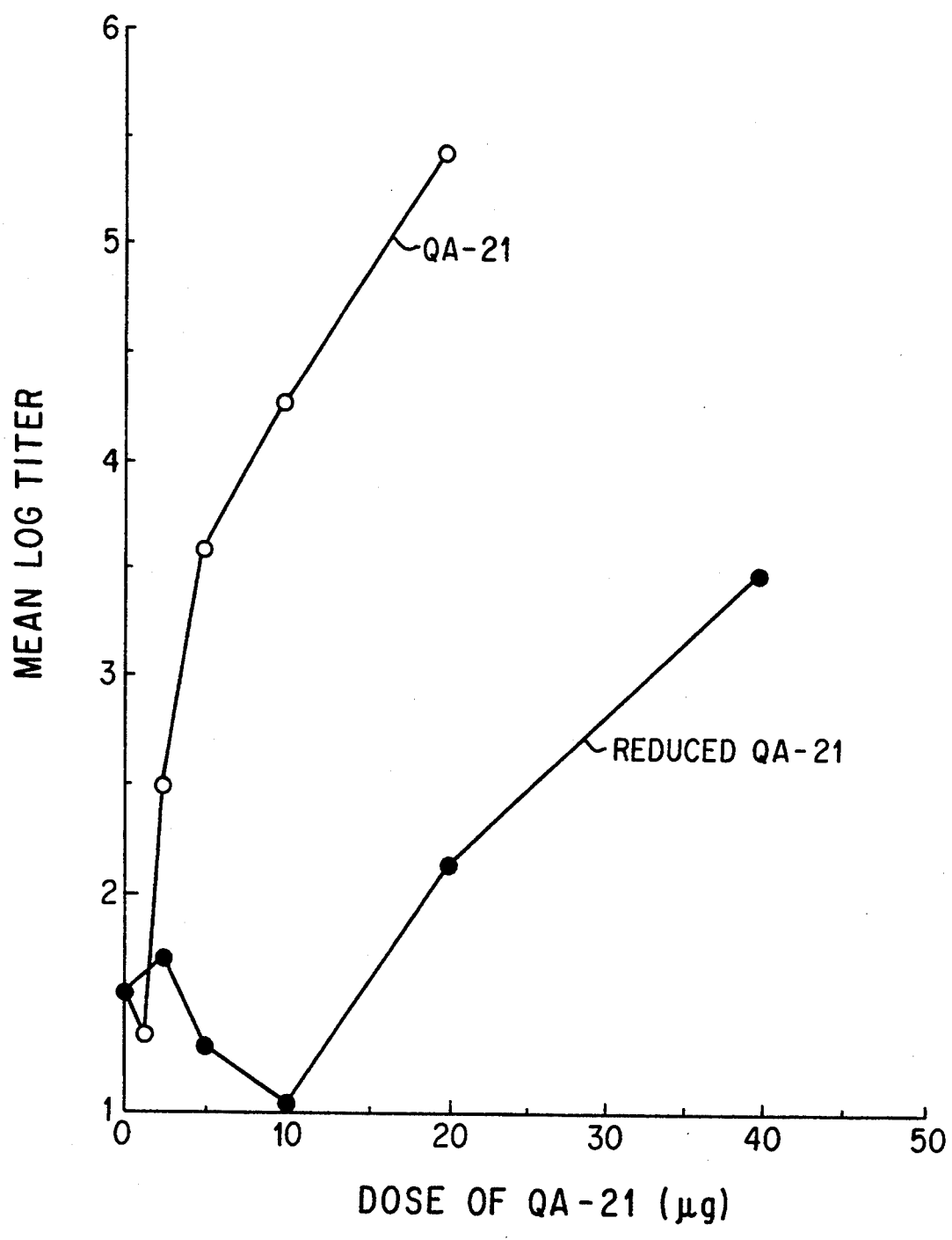
FIG. 12 depicts a graph showing the adjuvant activities of QA-21 (○) and QA-21 modified at the triterpene aldehyde by reduction to the corresponding methylene alcohol ( ).

Modified QA-21 saponins, as prepared above, were tested for adjuvant activity. C57 bl/6 mice (5 per group) were immunized subcutaneously with 25 μg ovalbumin and 10–50 μg QA-21 or one of its derivatives in saline. A booster immunization was given at day 14. Antibody response (total IgG) was tested by enzyme immunoassay after the second immunization. The two derivatives prepared by reductive alkylation at the triterpene aldehyde did not retain adjuvant activity at the doses tested (FIG. 11). The modified QA-21 in which the triterpene aldehyde was reduced to an alcohol retained some adjuvant activity, but with a higher minimum effective dose than QA-21 (FIG. 12). Results from similar experiments in which two booster immunizations were given at two week intervals are summarized in Table 2.

TABLE 2

| Adjuvant Activity of QA-21 and Derivatives | |
|---|---|
| Saponin (10 μg) administered with ovalbumin (10 μg) | Anti-ovalbumin IgG, Total (log titer) |
| none | 2.59 ± 0.81 |
| QA-21 | 4.06 ± 0.30 |
| QA-21-A-ethylamine[a] | 2.69 ± 0.59 |
| QA-21-A-ethylene diamine[a] | 2.68 ± 0.36 |
| QA-21-A-glycine[a] | 2.00 ± 0.19 |

[a]Modified at triterpene aldehyde.

EXAMPLE 4

Hemolytic Activity of Modified Saponins

The hemolytic assay provides a rough measure of the ability of a detergent to increase the uptake of pharmacologically active substances across mucous membranes by determining membrane permeabilization. Briefly, dilutions of the modified saponins are made on a round bottom, microliter plate with 1:2 dilutions in phosphate buffered saline in successive rows (100 μl/well). 10 μl normal sheep blood in Alsevers solution (Whittaker) was added to each well and mixed. Plates were incubated for one hour at room temperature followed by centrifugation of the plates in a Sorvall RT6000 to sediment unhemolyzed cells. Absence of hemolysis was determined by the presence of a pellet of unhemolyzed cells in the bottom of the well. Hemolytic activity is determined by the increase of release of hemoglobin from sheep red blood cells (measured as absorbance at 562 or 570 nm in the red blood cell supernatant).

Figure 1:
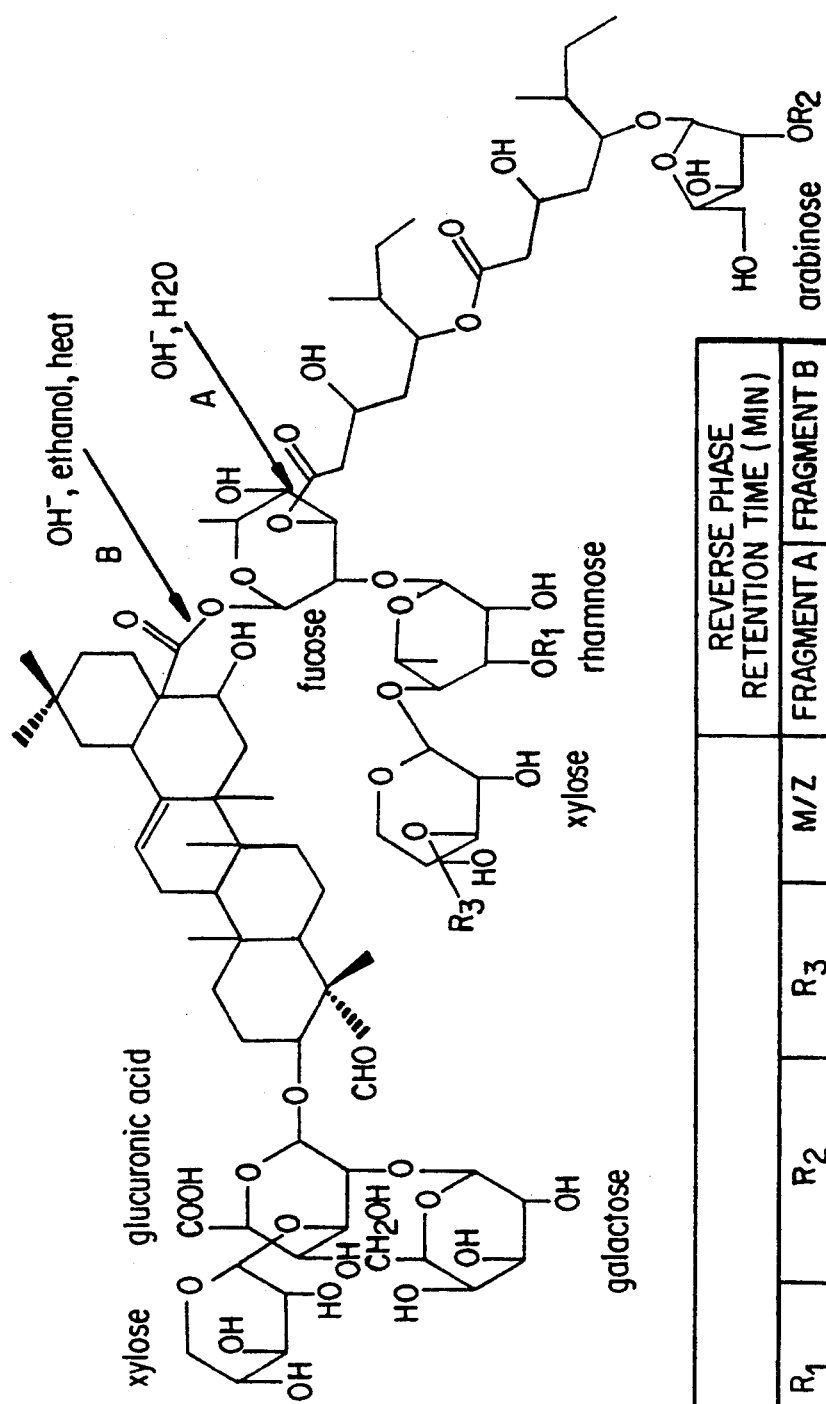
FIG. 1 depicts the structural relationships of QA-17, QA-18, and QA-21.
Figure 2A:
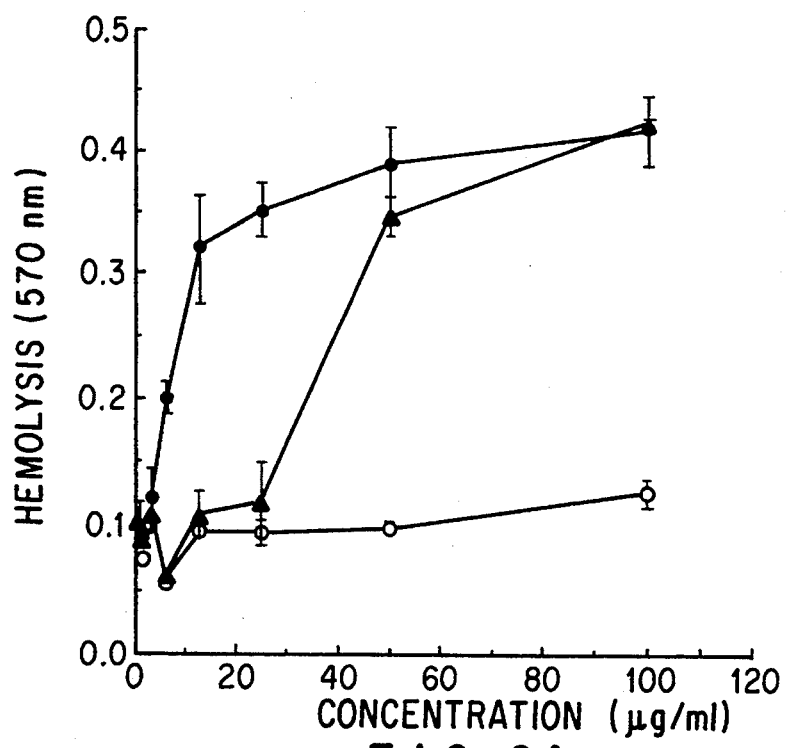
FIG. 2A depicts a graph showing the hemolytic activity of phosphate buffered saline, PBS, (○), QA-21 (●), and QA-21 (▲) wherein the aldehyde group is reduced to methylenealcohol.
Figure 2B:
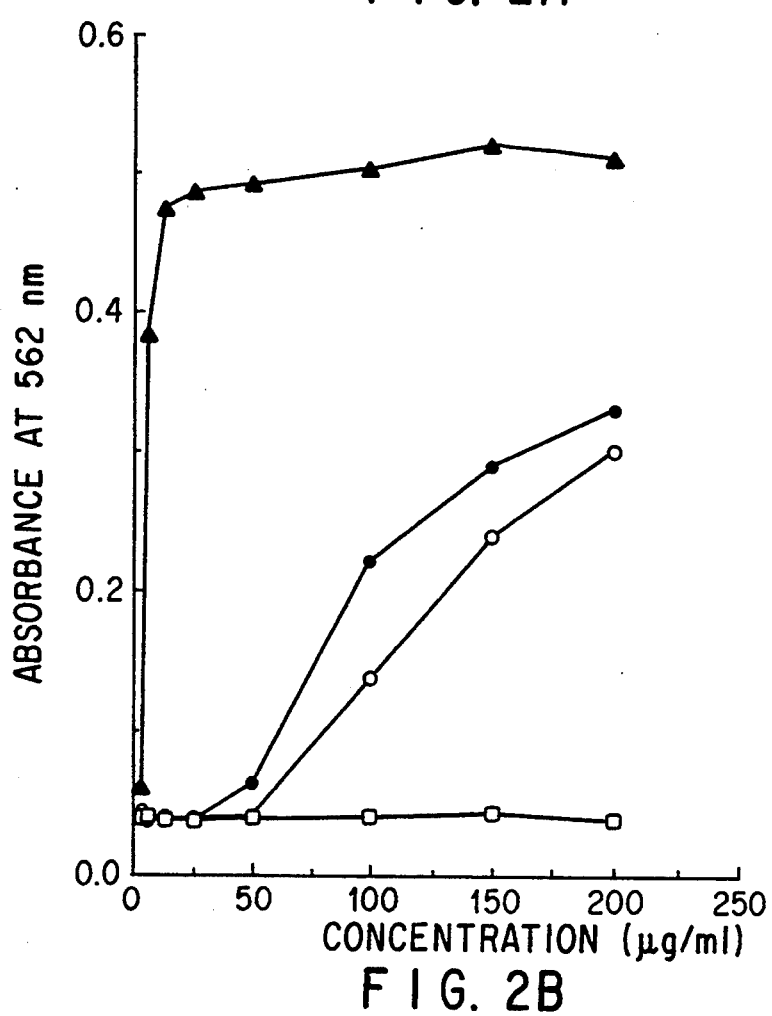
FIG. 2B depicts a graph showing the hemolytic activity of QA-18-H (○), QA-21-H (●), QA-7 (□), and QA-21 (▲).

As shown in FIG. 2, QA-21 substantially increases membrane permeabilization at very low concentrations. Reduced QA-21 also increases membrane permeabilization, but at a lower level and at higher concentrations compared to QA-21.

EXAMPLE 5

Ocular Administration of Insulin Increased by Modified Saponins

Protocol:

Male Sprague-Dawley rats were anesthetized with xylasine-ketamine and 30 minutes later (time 0), eye drops composed of saline plus or minus 0.4% insulin (100 U/ml) and one of the following saponins: Sigma crude saponin extracted from Gypsophilla Sigma Chemical Company, St. Louis, Mo.); crude saponin extracted from Quillaja; QA-21-H purified saponin hydrolytic derivative from QA-21. Typically, 20 μl of eye drops was delivered to one eye, but, occasionally, 20 μl was delivered to both eyes. Blood D-glucose levels were measured using an AccuCheck-II glucometer (Boehringer-Mannheim). Data represent the level of blood glucose at various times before and after eye drop administration. Each single line represents the data obtained from one experimental animal, except where indicated.

Results

Figure 3A:
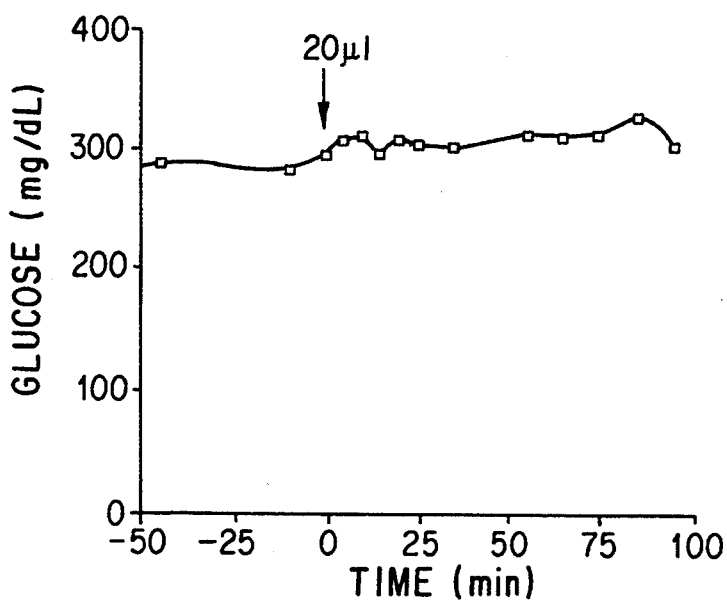
FIG. 3A depicts a graph showing blood glucose levels of rats after ocular administration of 20 μl of saline.
Figure 3B:
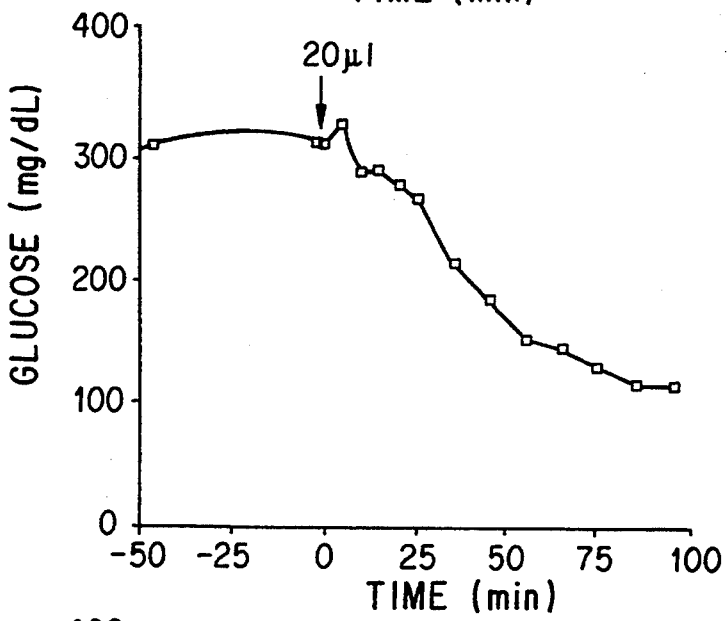
FIG. 3B depicts a graph showing blood glucose levels of a rat after ocular administration of 20 μl of 0.5% of a commercially available crude Gypsophilla saponin (Sigma Chemical Corporation)+0.4% porcine insulin.
Figure 3C:
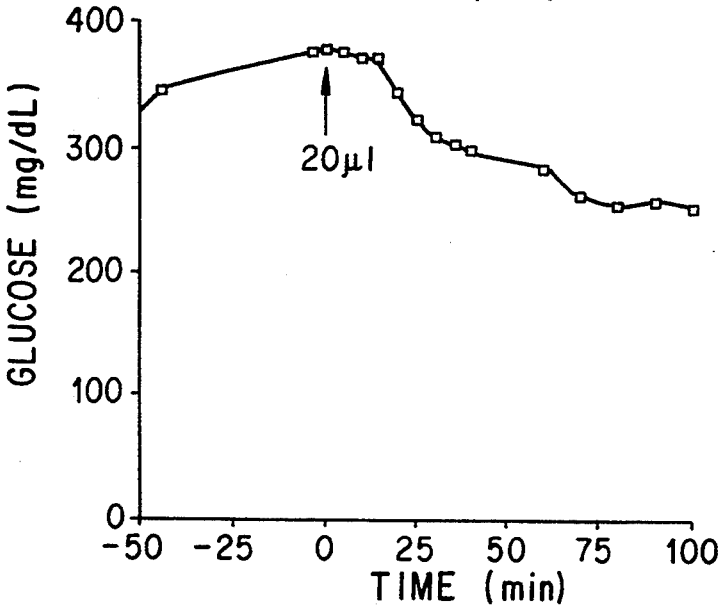
FIG. 3C depicts a graph showing blood glucose levels of a rat after ocular administration of 20 μl of 0.5% of crude Quillaja saponaria saponin (purified from an aqueous extract by ultrafiltration)+0.5% porcine insulin.

As shown in FIG. 3A, when saline was administered to the eyes of rats as a control, there was very little change in the blood glucose levels. However, when 0.5% of Sigma Gypsophilla saponin was coadministered with 0.4 % regular pork insulin, a significant hypoglycemic effect was observed. See FIG. 3B. When 0.5% of crude Quillaja saponin (unmodified) was coadministered with 0.4% regular pork insulin, a less significant reduction in glucose serum levels was obtained. See FIG. 3C.

FIG. 4 depicts a graph showing the effect of the ocular administration of a control solution of 0.1% pure saponin (without insulin) on the blood glucose levels of 3 male rats. As can be seen from the graph, no significant hypoglycemic effect could be observed in the absence of insulin.

FIG. 5 depicts a graph showing the results of the administration of 20 μl of 0.025% QA-21-H and 0.4% regular pork insulin on the blood glucose levels of three rats. As can be seen from the graph, a significant hypoglycemic effect was observed.

Figure 6:
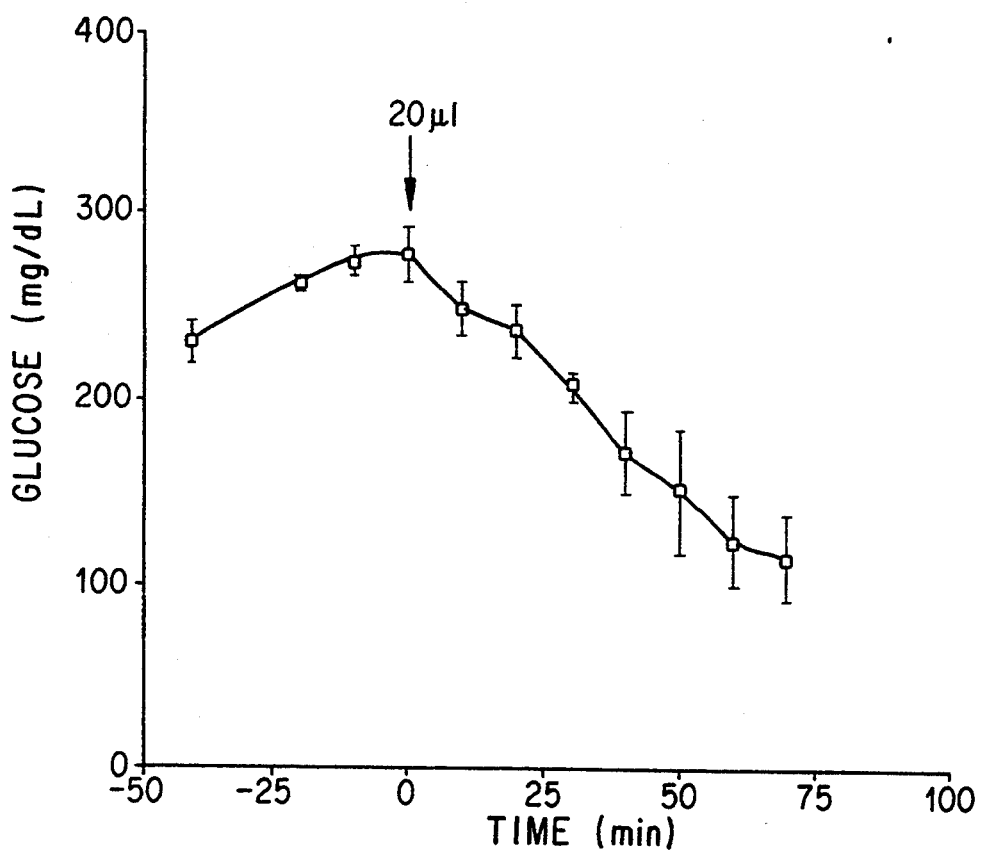
FIG. 6 shows a graph showing the results of the ocular administration of 0.05% QA-21-H and 0.4% regular pork insulin on the mean of the blood glucose levels of three male rats.

FIG. 6 depicts a graph showing a graph showing the results of the administration of 0.05% QA-21-H and 0.4% regular pork insulin on the blood glucose levels of three male rats. As can be seen from the graph, a significant hypoglycemic effect was observed.

Figure 7:
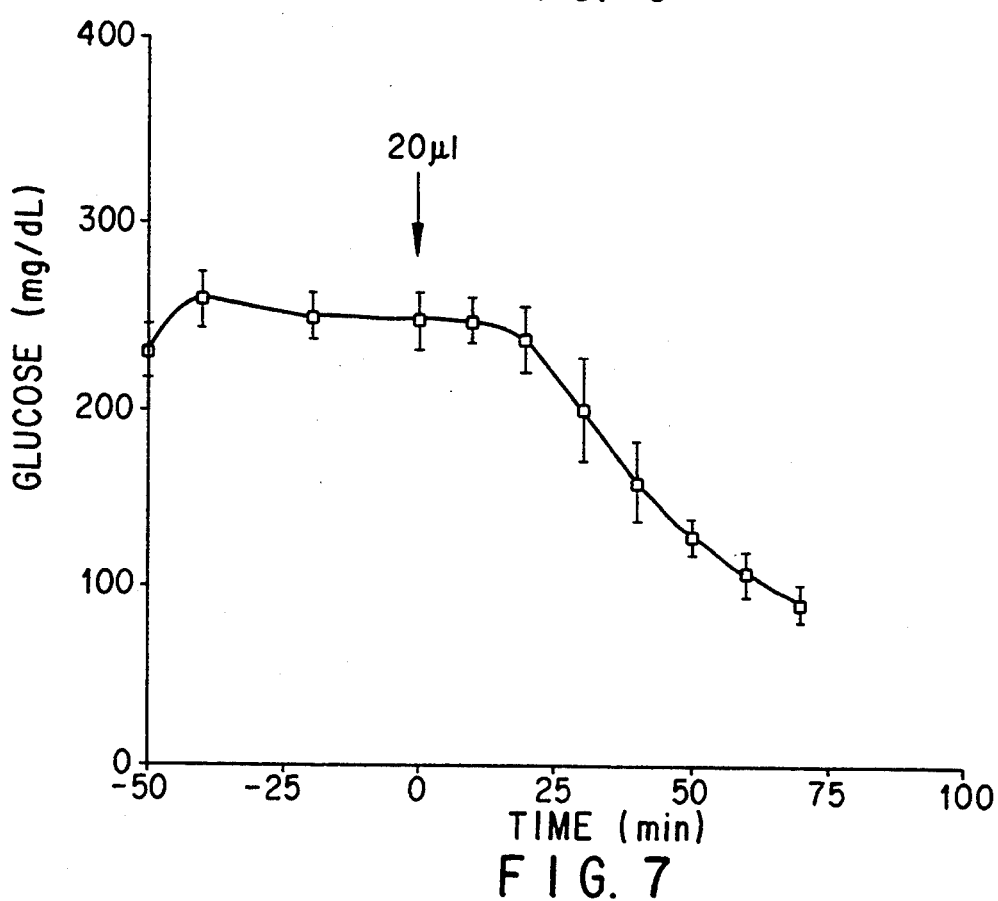
FIG. 7 depicts a graph showing the results of the ocular administration of 0.1% QA-21-H and 0.4% regular pork insulin on the mean of the blood glucose levels of four male rats.

FIG. 7 depicts a graph showing the results of the administration of 0.1% QA-21-H and 0.4% regular pork insulin on the blood glucose levels of four male rats. As can be seen from the graph, a significant hypoglycemic effect was observed.

Figure 8:
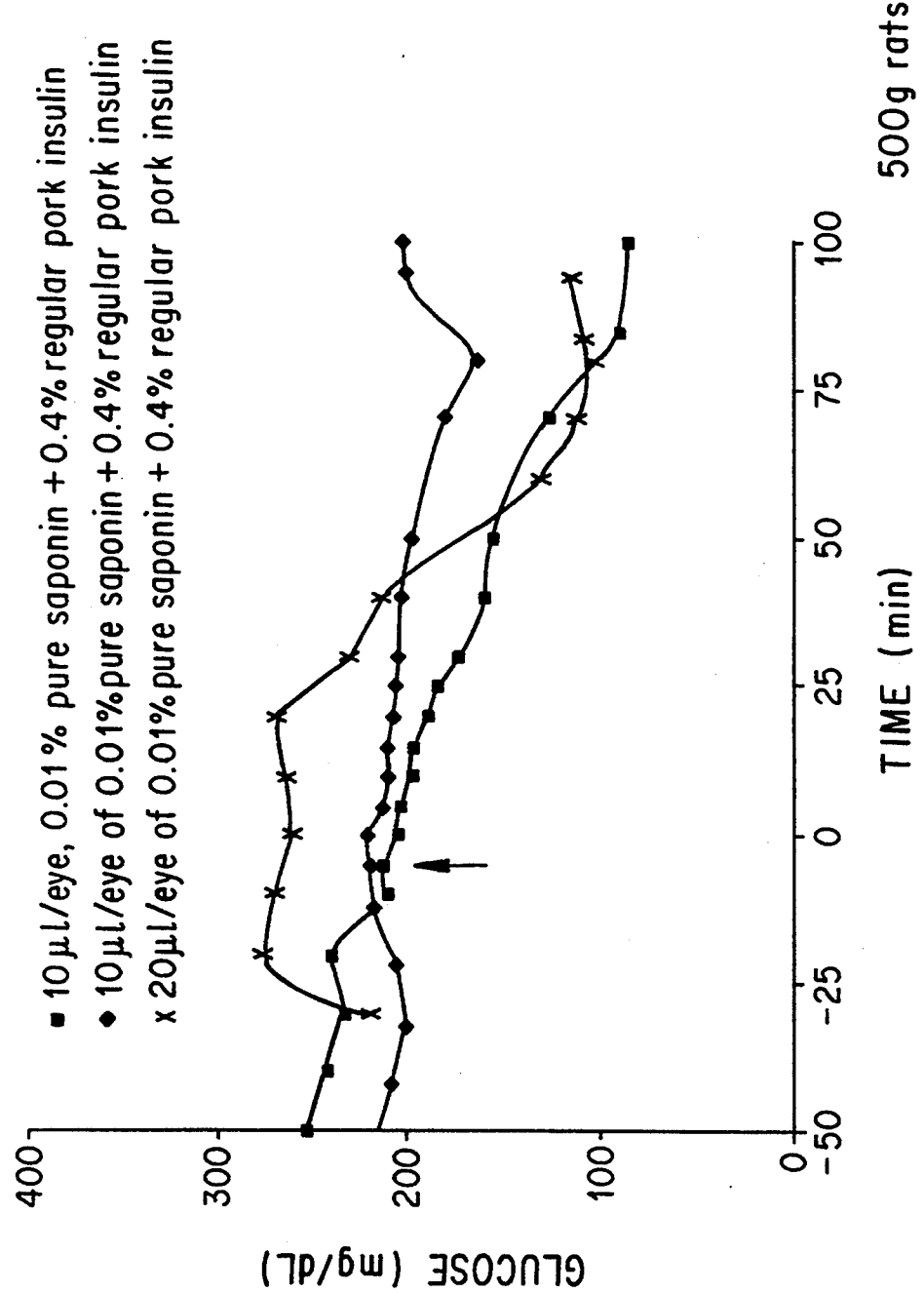
FIG. 8 depicts a graph showing the blood glucose lowering effect of the ocular administration of 10 μl/eye, 0.01% QA-21-H and 0.4% regular pork insulin to a first rat (■); 10 μl/eye of 0.01% pure QA-21-H and 0.4% regular pork insulin to a second rat (♦); and 20 μl/eye of 0.01% QA-21-H and 0.4% regular pork insulin to a third rat (x).

FIG. 8 depicts a graph showing the blood glucose lowering effect of the ocular administration of 10 μl/eye, 0.01% QA-21-H and 0.4 % regular pork insulin to a first rat; 10 μl/eye of 0.01% pure QA-21-H and 0.4% regular pork insulin to a second rat; and 20 μl/eye of 0.01% QA-21-H and 0.4% regular pork insulin to a third rat. The results show that even at 0.01 QA-21-H, some marginal transport of insulin was observed.

These experiments allow one to derive the following conclusions:

1. The effect of all the saponins tested on insulin absorption displayed a rapid onset, with maximal hypoglycemic action observed after 60 minutes.
2. Compared to Sigma saponin, Quillaja saponin was less potent at stimulating systemic absorption of insulin from eye drops, whereas QA-21-H was considerably more potent.
3. Ocular irritation decreased as the concentration of saponin decreased; 0.1% purified QA-21-H did cause ocular irritation, while 0.05% and 0.025% QA-21-H caused progressively less irritation; however, the two lower non-irritating doses were effective in inducing transport, indicating that this product can be used effectively for transport in the absence of irritation. Partially purified (crude) Quillaja saponin caused ocular irritation at 0.5%, a dose that was minimally effective in inducing transport, indicating that this crude product cannot be used effectively in absence of irritation.

EXAMPLE 6

Preparation of QA-21-H from QA-21

QA-21 (10 mg/ml in water) was subjected to alkaline hydrolysis in 0.1N sodium hydroxide for 15 minutes at ambient temperature. At the end of the incubation period, the pH was adjusted with glacial acetic acid to pH 4. The resulting primary hydrolysis product was isolated by preparative HPLC on Vydac $C_4$ (5$\mu$, 300 Å pore size, 1.0 cm internal diameter $\times$ 25 cm length) in a gradient of 20 to 50 % solvent B at a flow rate of 4 ml/minute and a UV detector setting of 214 nm (solvent A=0.15% TFA/water. solvent B=0.15% TFA/acetonitrile). QA-21-H (which eluted with a retention time of 23 minutes) was collected and lyophilized.

EXAMPLE 7

Preparation of QA-21-H, R from QA-21-H

QA-21-H (10 mg/ml in 10 mM phosphate buffer, pH 6.5, total of 38.2 mg) was incubated with 0.33M sodium borohydride for two hours at 4° C. to produce a product in which the triterpene aldehyde was reduced to an alcohol (designated QA-21-H,R). The residual sodium borohydride was separated from QA-21-H,R by dialysis through a 1000 daltons molecular weight cutoff dialysis membrane, using a 62.5 fold volume excess of water. The QA-21-H,R was retained by the dialysis membrane. The dialysis step was repeated three additional times. The dialyzed QA-21-H,R solution was lyophilized, yielding 28 mg.

EXAMPLE 8

Analysis of QA-21, QA-21-H, and QA-21-H,R

QA-21, QA-21-H, and QA-21-H,R were compared by analytic reverse phase HPLC (Dynamax $C_8$, 300 Å pore size, 5 micron particle size, 0.46 cm $\times$ 25 cm (i.d.- $\times$ length), 1 ml/min. flow rate, 30–45% solvent B /30 minutes (where solvent A=0.15% TFA in water and solvent B=0.15% TFA in acetonitrile). Comparative retention time for QA-21, QA-21-H, and QA-21-H,R in this particular system were determined to be 28.0 min., 10.4 min., and 10.3 min., respectively. QA-21-H, and QA-21-H,R were mixed and injected on HPLC, confirming that these yielded separate peaks.

Figure 13A:
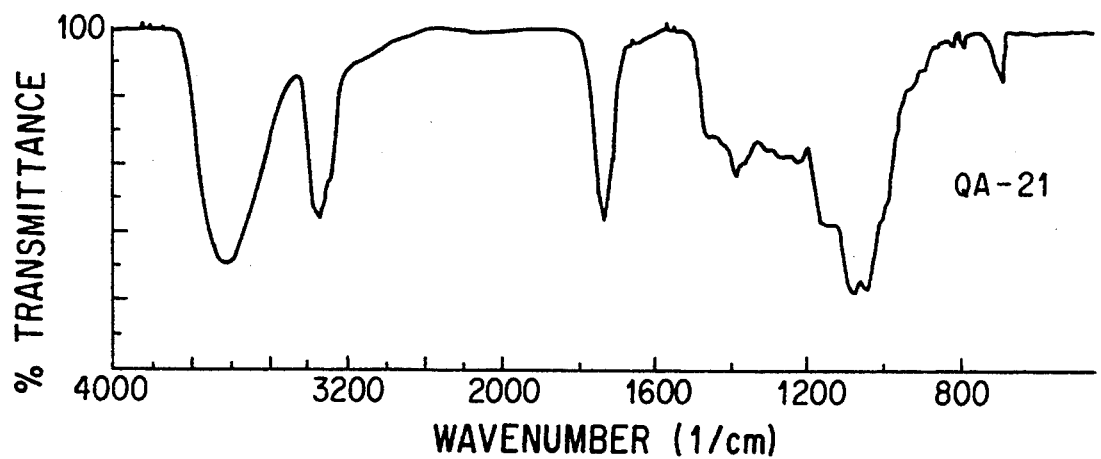
FIG. 13 shows infrared spectra of QA-21, QA-21-H, and QA-21-H,R.
Figure 13B:
Figure 13C:

Infrared spectra are shown in FIG. 13. Primary changes are observed in the C=O stretch region between 1600 to 1800, consistent with removal of two ester bonds from QA-21 during the preparation of QA-21-H and with elimination of the aldehyde in the preparation of QA-21-H,R.

Comparative FAB-MS spectra of QA-21-H, and QA-21-H,R yielded pseudomolecular ions of 1536 and 1538, respectively, consistent with the structure $[M+2H+Na]^+$ where $M=C_{69}H_{107}O_{36}$ for QA-21-H and $M=C_{69}H_{109}O_{36}$ for QA-21-H,R, indicating that reduction of the triterpene aldehyde to a methylenealcohol yielded the expected increase of 2 in the molecular weight.

EXAMPLE 9

Preparation of a Mixture of QA-18-H and QA-21-H

Figure 14A:
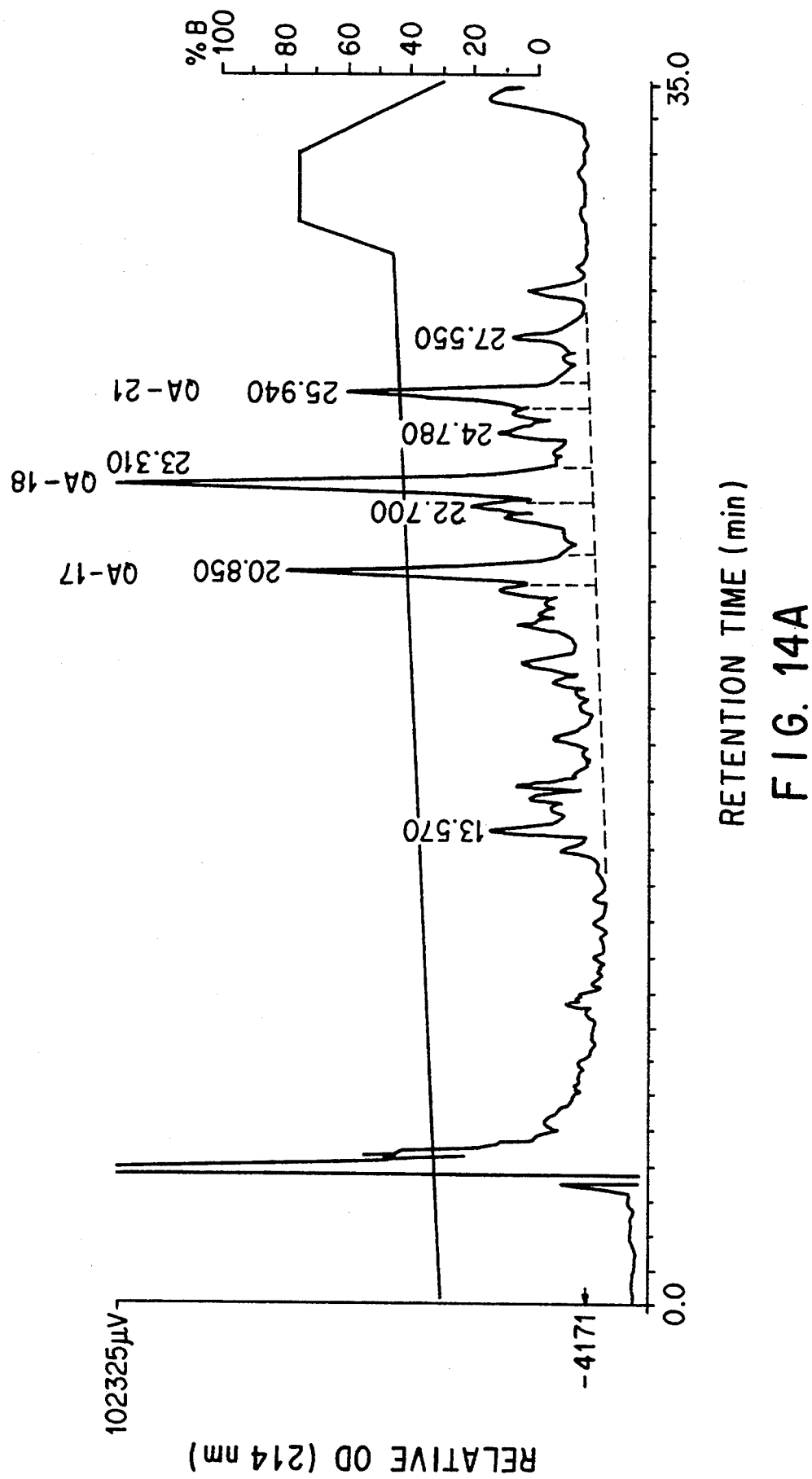
FIG. 14A shows an analysis by reverse phase HPLC of the total saponin fraction from Quillaja saponaria after partial purification by diafiltration.
Figure 14B:
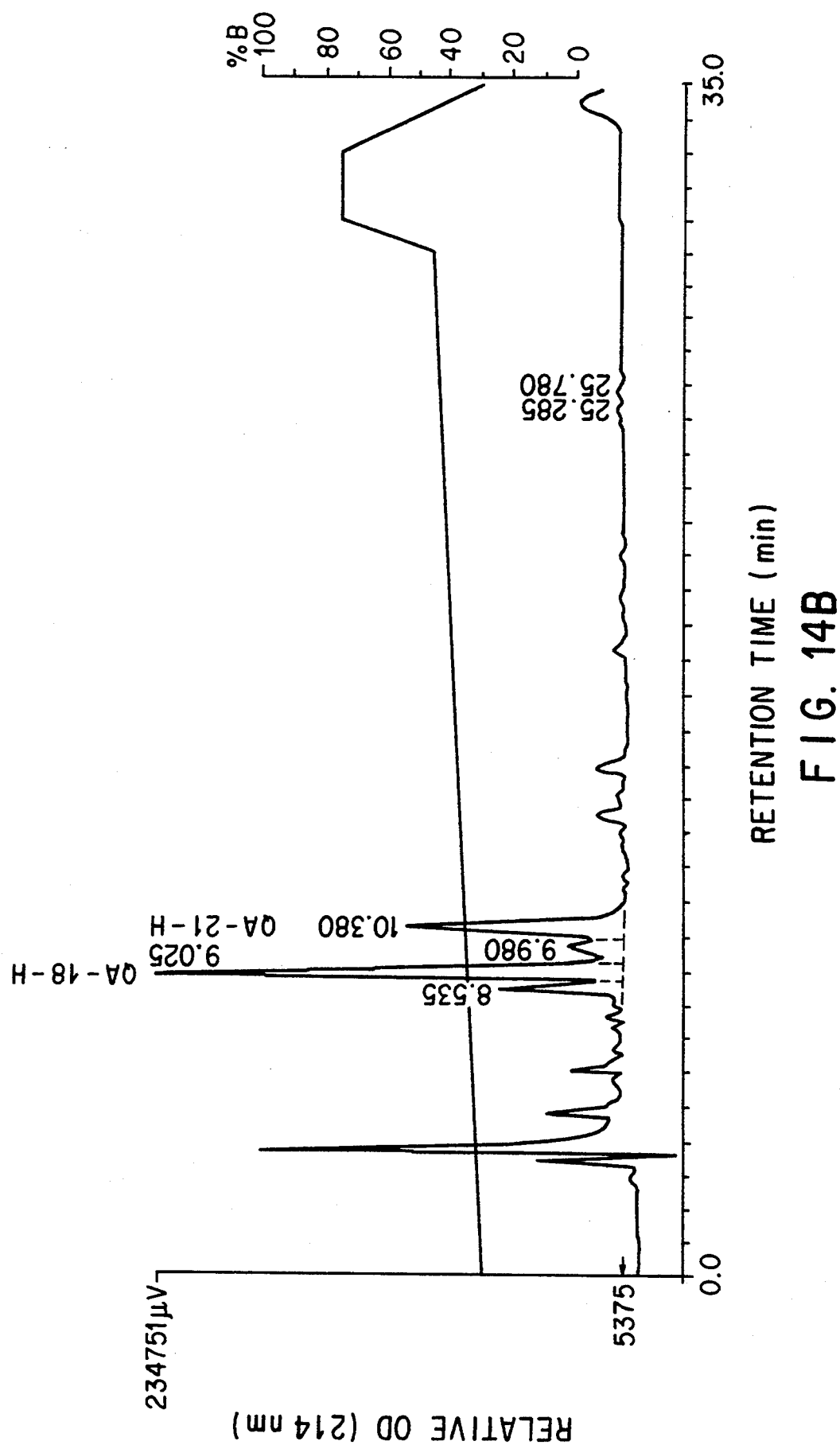
FIG. 14B shows the purity after hydrolysis and precipitation in 1-propanol and FIG. 14C shows the purity after silica chromatography.
Figure 14C:
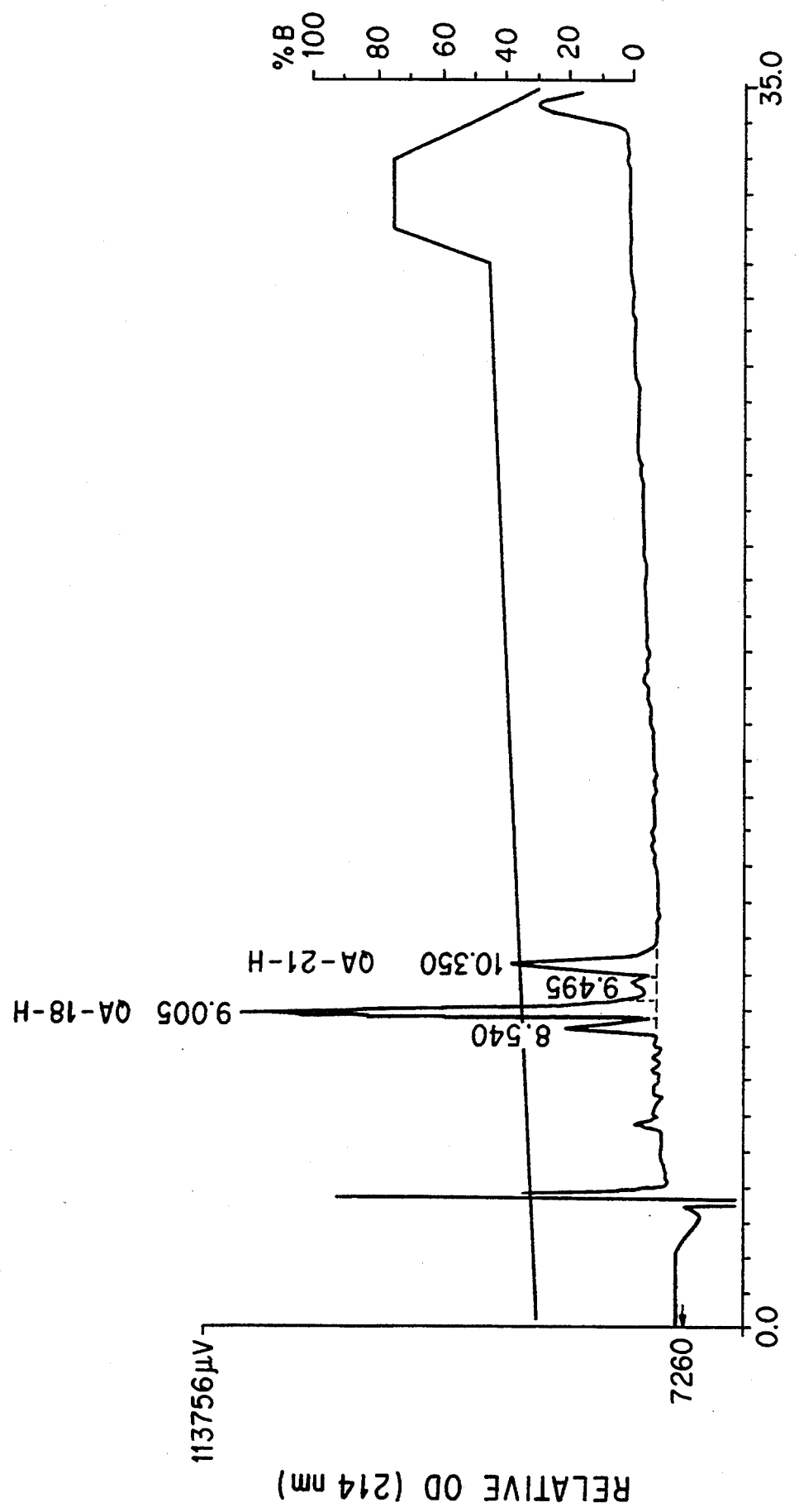

A crude mixture of *Quillaja saponaria* bark extract (dark brown in appearance) was partially purified by diafiltration through a 10,000 daltons molecular weight cartridge to an approximate purity of 8% QA-21 in the membrane retentate. A total of 400 mg of the 8% purity mixture was suspended in 12 ml of 90 % n-propanol. This solution was adjusted to 0.2N sodium hydroxide by addition of a 5N sodium hydroxide stock solution. This was vortexed and incubated for two hours at room temperature. The suspension was then centrifuged for five minutes at 50$\times$g, yielding a yellow colored supernatant and a dark brown grainy precipitate. This precipitate was washed three times with 12 ml of 90% propanol. The resulting pellet was redissolved in 12 ml water and adjusted to pH 3.8 with addition of glacial acetic acid. A total volume of 12 ml of n-propanol was added for a final propanol percent of approximately 50 %. This solution was then allowed to adsorb to two grams of silica (Lichroprep Si60) followed by removal of the solvent under a gentle stream of nitrogen. This preadsorbed silica was loaded evenly on top of a Lichroprep Si60 column (2.5 cm internal diameter $\times$ 14 cm height) equilibrated in 1-propanol. Approximately 1 column volume of 1-propanol was eluted through the column. This was followed by 3 column volumes of 85% 1-propanol, 2.5 column volumes of 80% 1-propanol, and 2.5 column volumes of 75% 1-propanol. QA-18-H and QA-21-H eluted together in a single pool with 75% 1-propanol. These were collected and lyophilized yielding 113 mg of a white powder. A total of 48 mg was dissolved in 0.6 ml of 20 mM acetic acid and adsorbed to a Vydac $C_{18}$ column (20–30$\mu$, 1 cm internal diameter $\times$ 10 cm length). The column was washed with 20 mM acetic acid (10 column volumes) and the peak containing QA-18-H and QA-21-H as a mixture was eluted with 30 % acetonitrile/20 mM acetic acid and lyophilized, yielding 39 mg. The purity was determined by analytical reverse phase HPLC to be approximately 52% QA-18-H and 22% QA-21-H. FIG. 14A shows an analysis by reverse phase HPLC of the total saponin fraction from *Quillaja saponaria* after partial purification by diafiltration; FIG. 14B shows the purity after hydrolysis and precipitation in 1-propanol and FIG. 14C shows the purity after silica chromatography.

EXAMPLE 10

Purification of QA-18-H and QA-21-H Directly from Hydrolyzed Crude Mixture

A total of 100 mg of diafiltered *Quillaja saponaria* bark extract was dissolved in 3 ml of 90% propanol and hydrolyzed as in Example 9. The brown pellet yielded after hydrolysis was redissolved in 5 ml of 30% acetonitrile/20 mM acetic acid. A total of 5 ml was loaded onto a column of Vydac $C_{18}$ (20–30$\mu$, 2.5 cm I.D. $\times$ 14 cm length) and was eluted with 30% acetonitrile/20 mM acetic acid.

Figure 15A:
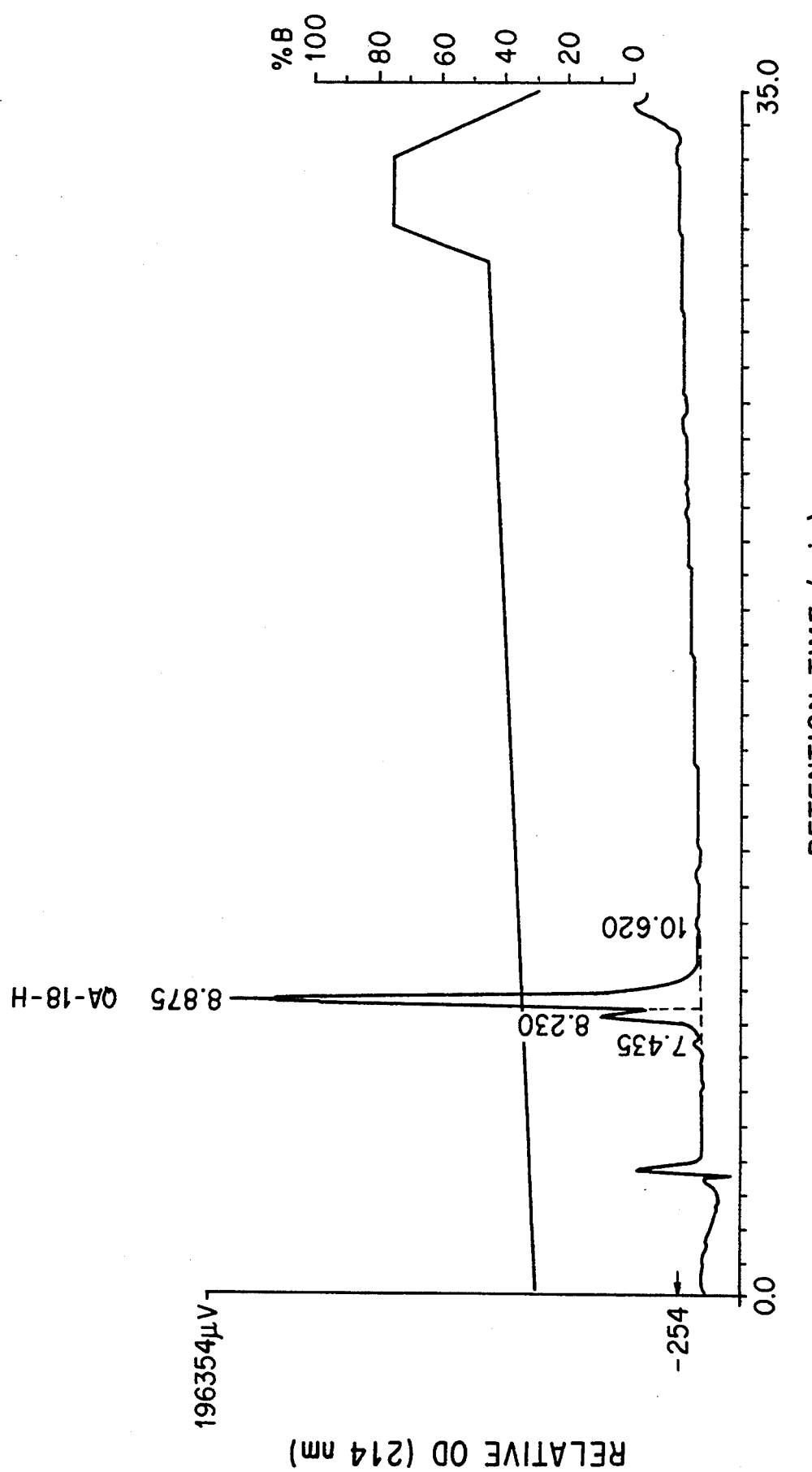
FIGS. 15A and 15B depict graphs showing the analyses of purified QA-18-H and QA-21-H, respectively, by reverse phase HPLC. (See Example 10).

Fractions 21–30 were pooled and lyophilized for QA-18-H, yielding 14.3 mg. This fraction was analyzed by reverse phase HPLC (FIG. 15A) to be 81.9% QA-18-H (retention time=8.68 min. on Dynamax $C_8$, 0.46 cm I.D. $\times$ 25 cm length, 300 Å pore size, 5 micron particle size, flow rate=1 ml/min, gradient=30–45% B/30 min where solvent A=0.15% TFA/water and solvent B=0.15% TFA/acetonitrile) and 16.6% of a preceding peak (retention time = 8.23 min.). These two peaks were isolated and were analyzed by HPLC comparison to a QA-18-H standard and by FAB-MS. The main peak was confirmed by HPLC analysis and FAB-MS to be QA-18-H. The preceding minor peak was shown to be 14 daltons molecular weight higher than QA-18-H, consistent with this being a closely related compound to QA-18-H. Hence, QA-18-H could be purified directly from a hydrolyzed crude mixture that originally contained QA-17 and QA-18 (precursors of QA-18-H) as well as directly from hydrolyzed purified QA-17 and QA-18.

Figure 15B:
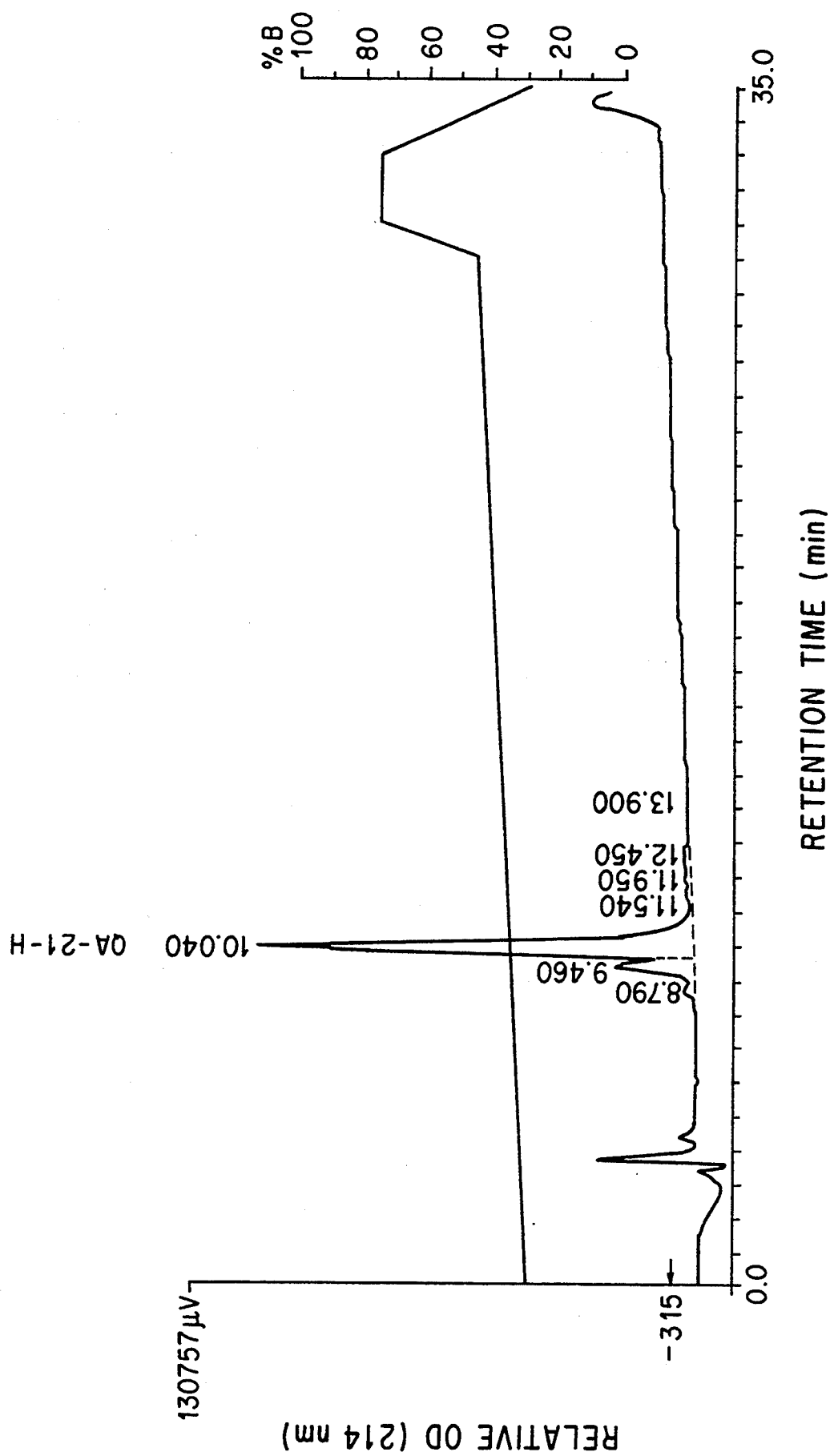

Fractions 31–41 were pooled and lyophilized for QA-21-H, yielding 7.7 mg of QA-21-H. Analysis by reverse phase HPLC (FIG. 15B) showed that the product consisted of 78.7% QA-21-H (retention time = 10.04 min.) and 13.3% of a preceding peak (retention time = 9.46 min.). These two peaks were isolated and the main peak was analyzed by analytic reverse phase HPLC comparison to QA-21-H standard run on the same day to confirm its identity as QA-21-H. Hence, QA-21-H could be purified directly from a hydrolyzed crude mixture that originally contained QA-21 as well as from hydrolyzed purified QA-21.

EXAMPLE 11

Delivery of Insulin by Eye Drop Route to Test Effect of Deletion of Fatty Acid and Reduction of Triterpene Aldehyde on Delivery Molecules The activity of QA-21 (unmodified), QA-21-H (fatty acid domain deleted), and QA-21-H,R (fatty acid domain deleted and triterpene aldehyde reduced to an alcohol) was tested for delivery of insulin through ocular delivery in the anesthetized rat model described supra. A total volume of 20 μl of insulin and varying doses of test delivery agents (at concentrations of 0.01%, 0.025%, 0.05%, and 0.1%) was delivered to both eyes (10 μl per eye). Glucose levels were monitored at frequent time intervals in the post-administration period.

Figure 16:
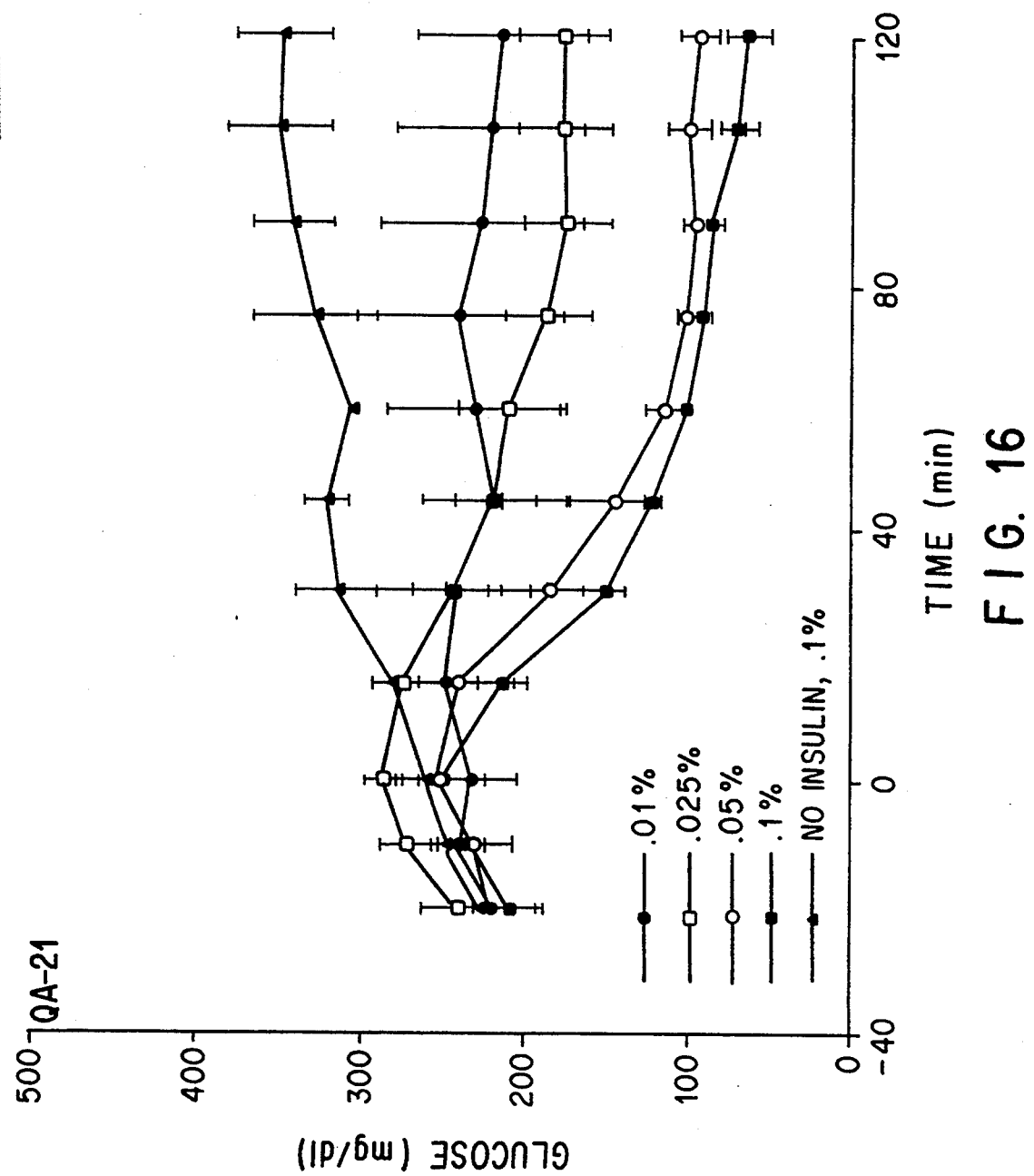
FIG. 16 shows the effect of QA-21 concentration on ocular delivery of insulin.
Figure 17:
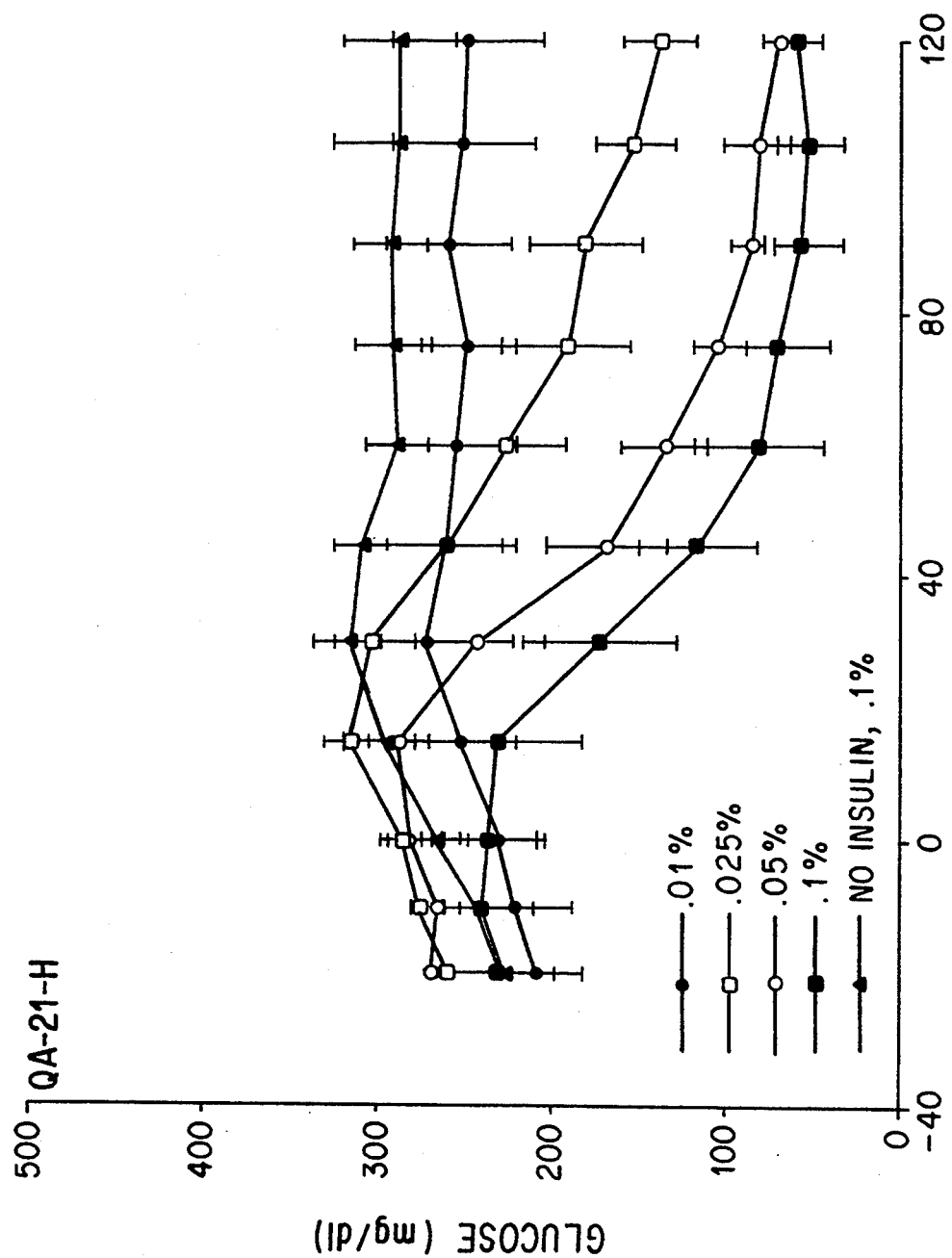
FIG. 17 shows the effect of QA-21-H concentration on ocular delivery of insulin.
Figure 18:
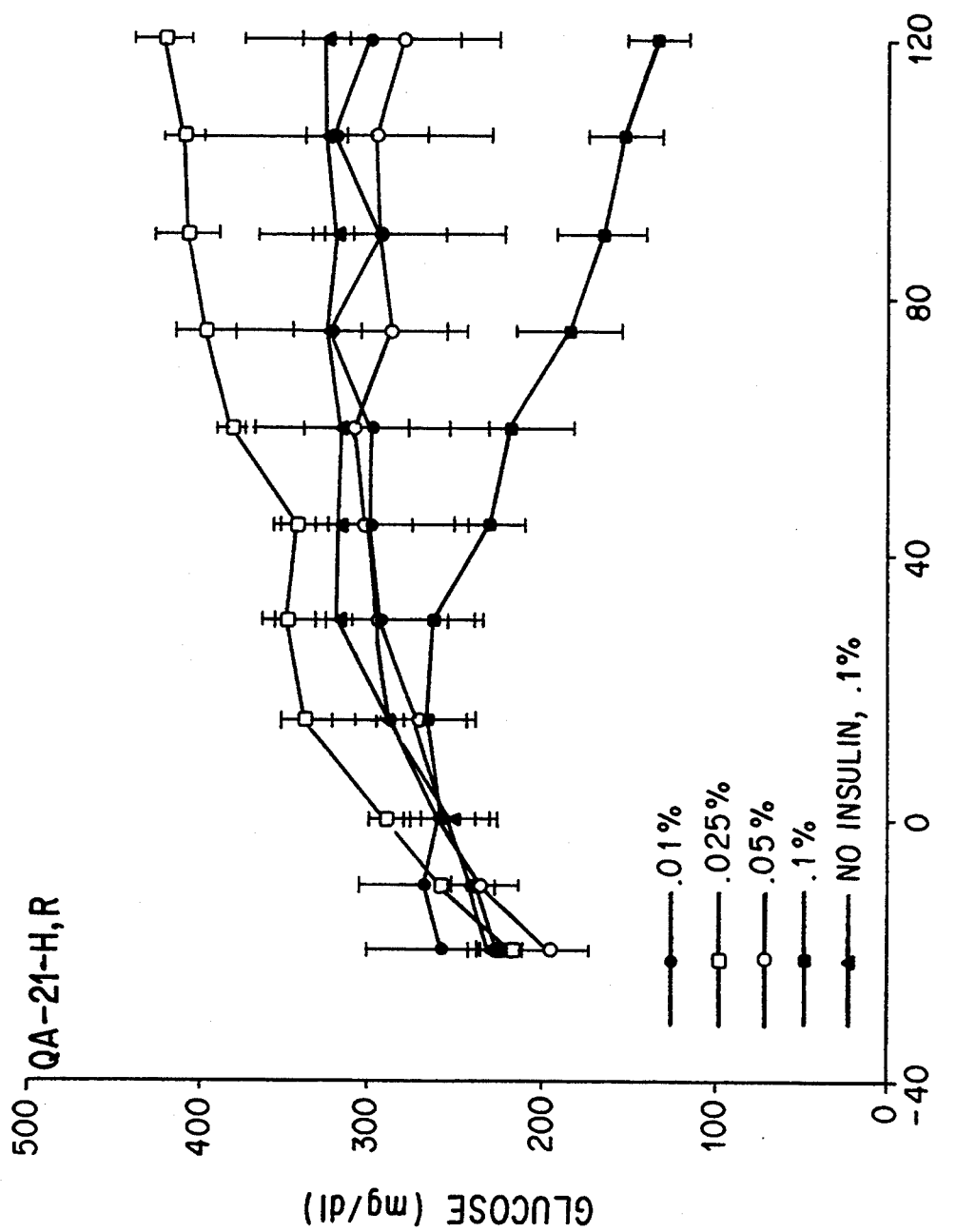
FIG. 18 shows the effect of QA-21-H,R concentration on ocular delivery of insulin.

FIG. 16 shows the effect of QA-21 concentration on ocular delivery of insulin. FIG. 17 shows the effect of QA-21-H concentration on ocular delivery of insulin. FIG. 18 shows the effect of QA-21-H,R concentration on ocular delivery of insulin. The results are listed as a mean and standard deviation of the results from three rats at each concentration. Control formulations containing of 0.1% test delivery agent, but no insulin, did not stimulate a reduction of glucose concentration, indicating that none of the three test delivery agents caused a non-insulin dependent drop in glucose levels. Insulin transport was observed with QA-21-H,R only at a concentration of 0.1%. However, transport was observed with QA-21 and QA-21-H at concentrations of 0.025%. No effect was observable at 0.01%.

Figure 19:
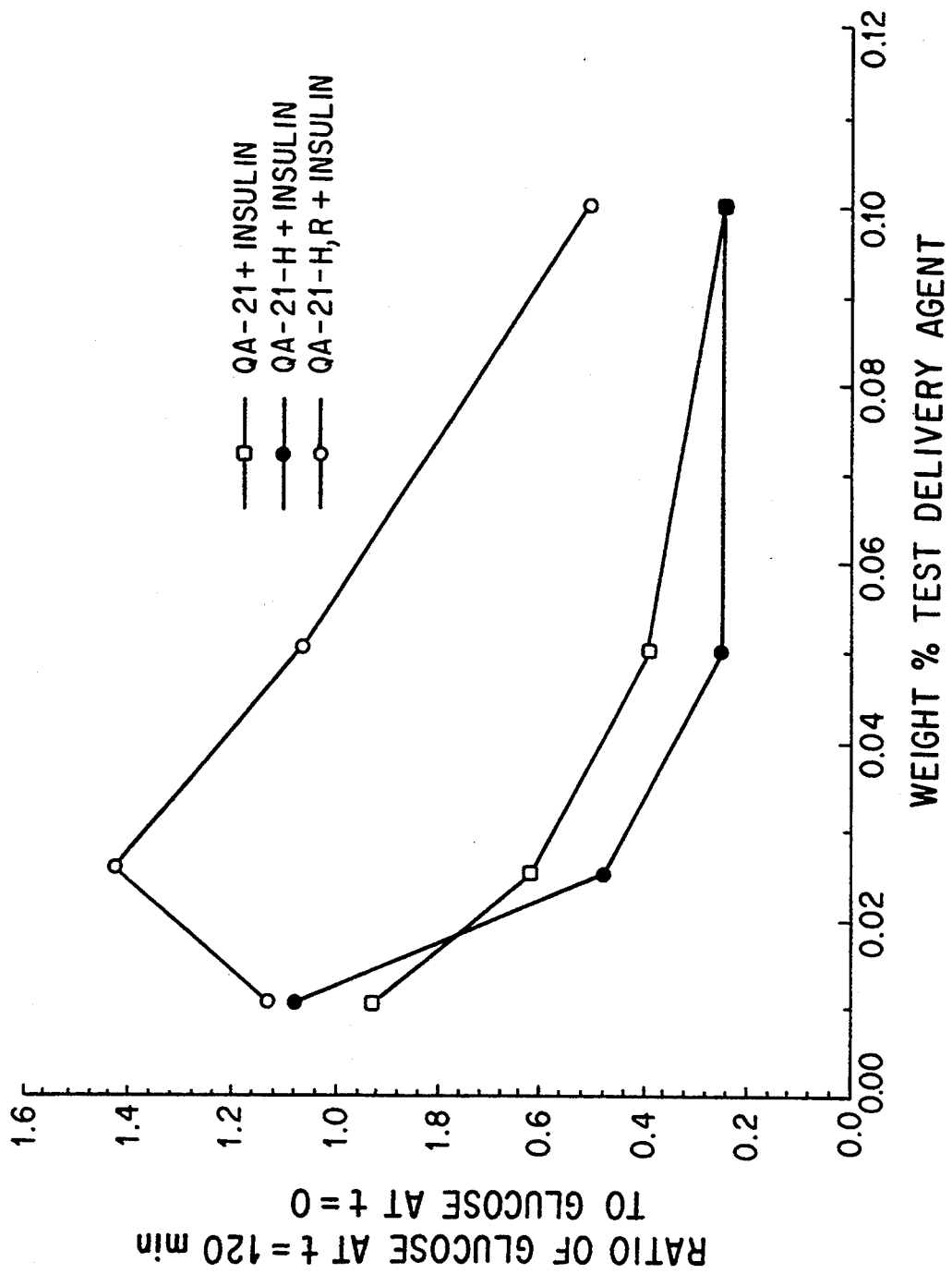
FIG. 19 shows the ratio of glucose levels at 120 minutes post-administration to glucose levels at time=0 (time of administration) as a function of concentration of QA-21, QA-21-H, and QA-21-H,R.

FIG. 19 shows the ratio of glucose levels at 120 minutes post-administration to glucose levels at time=0 (time of administration) as a function of concentration of QA-21, QA-21-H, and QA-21-H,R. The results indicate that QA-21 and QA-21-H appear to be equally potent in enhancing insulin transport. Hence, deletion of the fatty acid domain did not seem to affect transport activity. The QA-21-H,R was also able to promote ocular transport of insulin although higher concentrations were required, suggesting that the reduction of the triterpene aldehyde decreased (but did not eliminate) the transport activity.

EXAMPLE 12

Delivery of Insulin by the Nasal Route

Test of QA-21-H, QA-18-H, and mixture of QA-18-H AND QA-21-H as Delivery Agents

Figure 20:
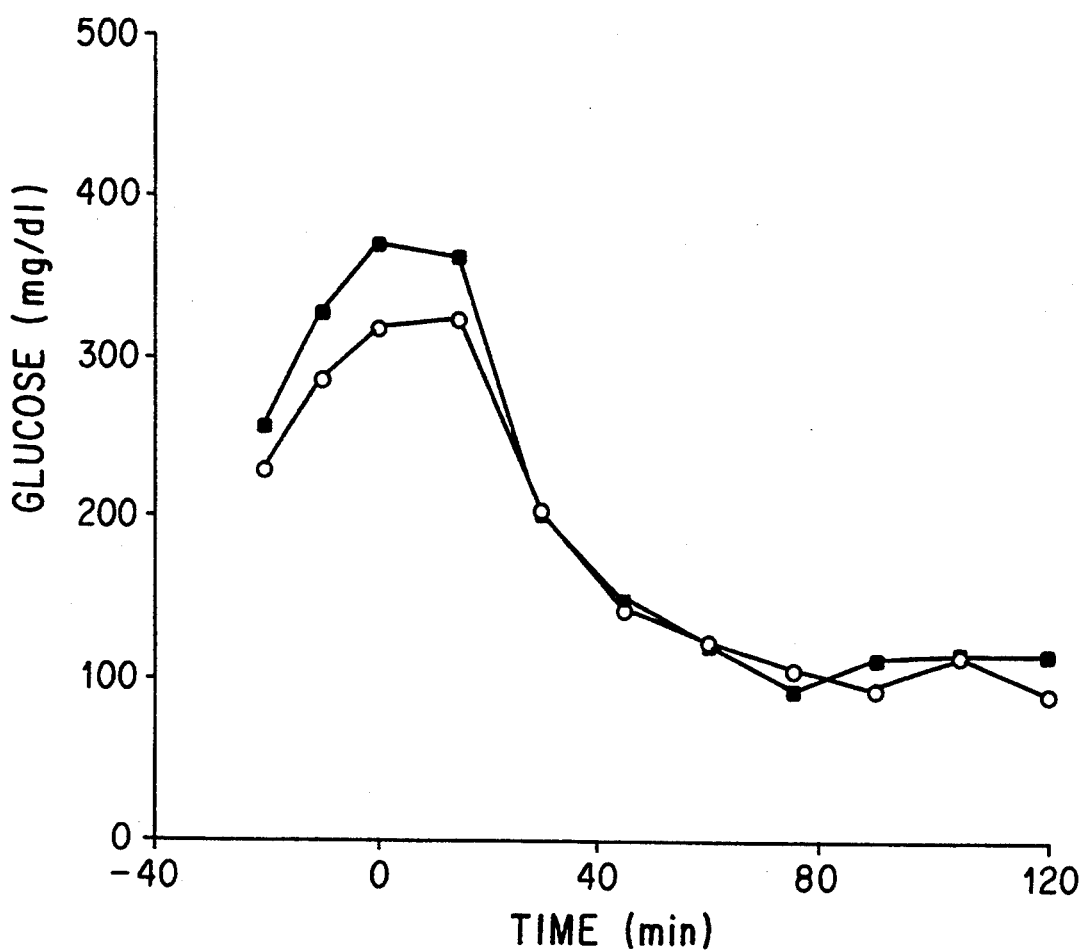
FIG. 20 shows the effect of QA-21-H on nasal delivery of insulin into rats.

FIG. 20 shows the effect of QA-21-H on nasal delivery of insulin into rats. A total of 20 μl of 0.05% QA-21-H and 0.2% insulin was administered to the right nostril of two rats at 0 and 5 minutes. Serum glucose levels were monitored before and after administration.

Figure 21:
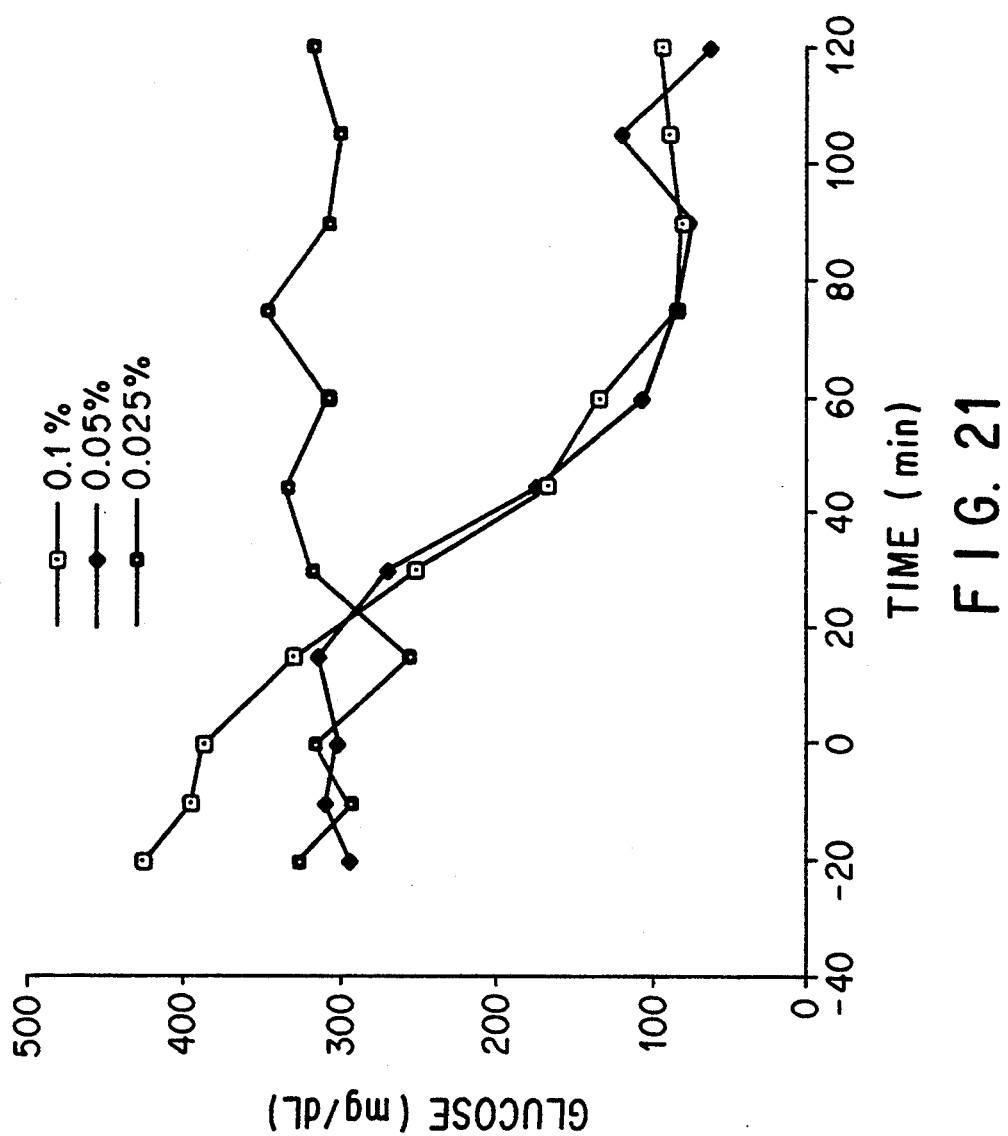
FIG. 21 shows the effect of QA-18-H on nasal delivery of insulin into rats.

FIG. 21 shows the effect of QA-18-H (prepared as described above) on nasal delivery of insulin. It was shown to be effective at 0.1% and 0.05%, but lost potency for transport at 0.025%.

Figure 22:
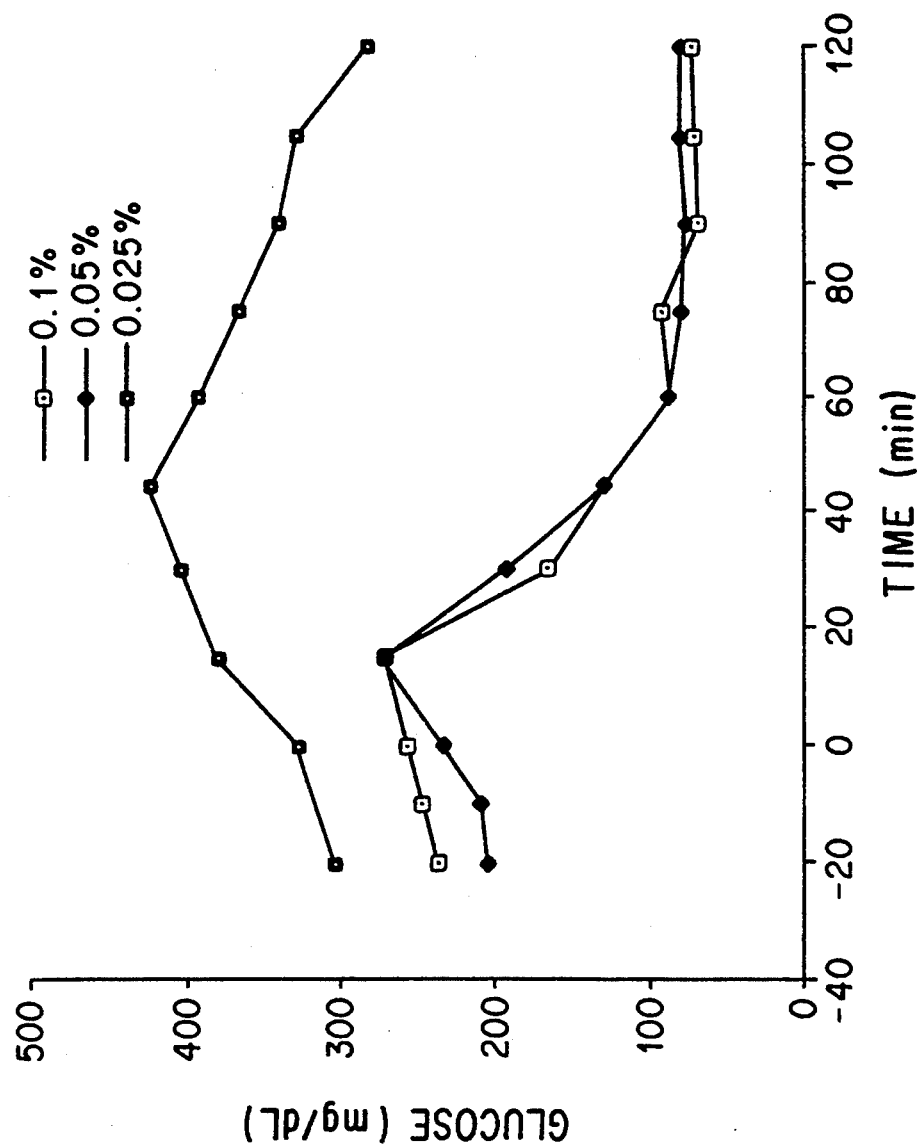
FIG. 22 shows the effect of a mixture of QA-18-H and QA-21-H on nasal delivery of insulin into rats.

FIG. 22 shows the effect of a mixture of QA-18-H and QA-21-H (prepared as described above) on nasal delivery of insulin. The mixture tested contained approximately 52% QA-18-H and 22% QA-21-H with the remainder being closely related molecules. It was effective at 0.1% and 0.05%, but lost most of the potency for transport at 0.025%.

The nasal delivery data on QA-21-H (shown above to be effective at increasing transport through the ocular route) suggest that these molecules are effective in other delivery routes, as well. Although QA-18-H and QA-18-H, QA-21-H mixture were not tested via the ocular route, their efficacy at increasing delivery through the nasal route indicates their potential for increasing delivery through other mucosal membranes.

From the foregoing description, one skilled in the art can easily ascertain the essential characteristics of this invention, and without departing from the spirit and scope thereof, can make various changes and modifications of the invention to adapt it to various usages and conditions, without undue experimentation.

What is claimed is:

1. A composition comprising a chemically modified saponin or a fraction thereof obtainable from a crude *Quillaja saponaria* extract, wherein the chemically modified saponin or fraction thereof comprises at least one of QA-17, QA-18, QA-21, QA-21-V1 or QA-21-V2 and wherein the chemical modification of the saponin or fraction thereof consists of
   (1) the reduction of the triterpene aldehyde group of QA-17, QA-18, QA-21, QA-21-V1 and QA-21-V2 to a methylenealcohol or a methyleneamino group; alone or in combination with
   (2) the hydrolysis of the fatty acid arabinose moiety or fatty acid arabinose-rhamnose moiety of QA-17, QA-18, QA-21, QA-21-V1 and QA-21-V2 to give the corresponding glycoside fragment.

2. The composition of claim 1, wherein said saponin or fraction thereof is QA-17, wherein the aldehyde group is reduced to methylenealcohol.

3. The composition of claim 1, wherein said saponin or fraction thereof is QA-18, wherein the aldehyde group is reduced to methylenealcohol.

4. The composition of claim 1, wherein said saponin or fraction thereof is QA-21, wherein the aldehyde group is reduced to methylenealcohol.

5. The composition of claim 1, wherein said saponin or fraction thereof is QA-21-V1, wherein the aldehyde group is reduced to methylenealcohol.

6. The composition of claim 1, wherein said saponin or fraction thereof is QA-21-V2, wherein the aldehyde group is reduced to methylenealcohol.

7. The composition of claim 1, wherein said saponin or fraction thereof is QA-17, wherein the aldehyde group is reduced to a methyleneamino group.

8. The composition of claim 1, wherein said saponin or fraction thereof is QA-18, wherein the aldehyde group is reduced to a methyleneamino group.

9. The composition of claim 1, wherein said saponin or fraction thereof is QA-21, wherein the aldehyde group is reduced to a methyleneamino group.

10. The composition of claim 1, wherein said saponin or fraction thereof is QA-21-V1, wherein the aldehyde group is reduced to a methyleneamino group.

11. The composition of claim 1, wherein said saponin or fraction thereof is QA-21-V2, wherein the aldehyde group is reduced to a methyleneamino group.

12. The composition of any one of claims 7–11, wherein said methyleneamino group is $-CH_2-N(R)-R''$, wherein R is hydrogen, R'' is selected from the group consisting of hydrogen, $C_1-C_8$ alkyl, $C_2-C_{12}$ alkylaminoalkyl, allyl, aralkyl, $C_3-C_8$ cycloalkyl, aryl and a group having the formula

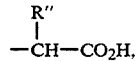

wherein R'' is hydrogen, $C_1-C_4$ alkyl, or $C_1-C_4$ alkyl substituted by phenyl, hydroxyphenyl, indolyl, mercapto, $C_1-C_4$ alkylthio, hydroxy, carboxy, amino, guanidino, imidazolyl or carbamyl; or wherein R and R'' together form a pyrrolidinyl or piperidinyl ring.

13. A composition comprising a chemically modified saponin or a fraction thereof obtainable from a crude *Quillaja saponaria* extract, wherein the chemically modified saponin or fraction thereof comprises at least one of QA-17, QA-18, QA-21, QA-21-V1 or QA-21-V2, and wherein the chemical modification of the saponin or fraction thereof consists of the hydrolysis of the fatty acid arabinose moiety or fatty acid arabinose-rhamnose moiety of QA-17, QA-18, QA-21, QA-21-V1 and QA-21-V2 to give the corresponding glycoside fragment in combination with the reduction of the triterpene aldehyde group of QA-17, QA-18, QA-21, QA-21-V1 and QA-21-V2 to a methylenealcohol or a methyleneamino group.

14. The composition of claim 13, wherein said saponin or fraction thereof is hydrolyzed QA-18, wherein the aldehyde group is reduced to methylenealcohol.

15. The composition of claim 13, wherein said saponin or fraction thereof is hydrolyzed QA-21, wherein the aldehyde group is reduced to methylenealcohol.

16. The composition of claim 13, wherein said saponin or fraction thereof is hydrolyzed QA-21-V1, wherein the aldehyde group is reduced to methylenealcohol.

17. The composition of claim 13, wherein said saponin or fraction thereof is hydrolyzed QA-21-V2, wherein the aldehyde group is reduced to methylenealcohol.

18. The composition of claim 13, wherein said saponin or fraction thereof is hydrolyzed QA-18, wherein the aldehyde group is reduced to a methyleneamino group.

19. The composition of claim 13, wherein said saponin or fraction thereof is hydrolyzed QA-21, wherein the aldehyde group is reduced to a methyleneamino group.

20. The composition of claim 13, wherein said saponin or fraction thereof is hydrolyzed QA-21-V1, wherein the aldehyde group is reduced to a methyleneamino group.

21. The composition of claim 13, wherein said saponin or fraction thereof is hydrolyzed QA-21-V2, wherein the aldehyde group is reduced to a methyleneamino group.

22. The composition of any one of claims 18–21, wherein said methyleneamino group is $-CH_2-N(R)-R''$, wherein R is hydrogen; R'' is selected from the group consisting of hydrogen, $C_1-C_8$ alkyl, $C_2-C_{12}$ alkylaminoalkyl, allyl, aralkyl, $C_3-C_8$ cycloalkyl, aryl and a group having the formula

wherein R'' is hydrogen, $C_1-C_4$ alkyl, or $C_1-C_4$ alkyl substituted by phenyl, hydroxyphenyl, indolyl, mercapto, $C_1-C_4$ alkylthio, hydroxy, carboxy, amino, guanidino, imidazolyl or carbamyl; or wherein R and R'' together form a pyrrolidinyl or piperidinyl ring.

* * * * *